US007625698B2

(12) United States Patent
Barendse

(10) Patent No.: US 7,625,698 B2
(45) Date of Patent: Dec. 1, 2009

(54) DNA MARKERS FOR MEAT TENDERNESS

(75) Inventor: William John Barendse, Bellbowrie (AU)

(73) Assignees: Commonwealth Scientific and Industrial Research Organisation, Campbell (AU); The State of Queensland Through Its Department of Primary Industries, Brisbane (AU); The University of New England, Armidal (AU); The State of New South Wales Through Its Department of Agriculture, Orange (AU); Meat & Livestock Australia Limited, North Sydney (AU)

( * ) Notice: Subject to any disclaimer, the term of this patent is extended or adjusted under 35 U.S.C. 154(b) by 259 days.

(21) Appl. No.: 10/467,665

(22) PCT Filed: Feb. 8, 2002

(86) PCT No.: PCT/AU02/00122

§ 371 (c)(1),
(2), (4) Date: Jan. 13, 2004

(87) PCT Pub. No.: WO02/064820

PCT Pub. Date: Aug. 22, 2002

(65) Prior Publication Data

US 2004/0115678 A1    Jun. 17, 2004

(30) Foreign Application Priority Data

Feb. 9, 2001    (AU)    ..................................... PR2975

(51) Int. Cl.
*C12Q 1/68*    (2006.01)
*C07H 21/04*    (2006.01)
*C12P 19/34*    (2006.01)
(52) U.S. Cl. ........................... 435/6; 536/24.3; 435/91.2
(58) Field of Classification Search ........................ None
See application file for complete search history.

(56) References Cited

FOREIGN PATENT DOCUMENTS

| WO | 98/38514 A1 | 9/1998 |
| WO | 07/012119 A1 | 2/2007 |
| WO | 07/053891 A1 | 5/2007 |
| WO | 08/034186 A1 | 3/2008 |

OTHER PUBLICATIONS

Chung et al, The Ohio State Univeristy Bulletin extension research, Circular 170-99, ohioline.edu/sc170/sc170_3.html, 1999 pp. 1-9.*
Green et al, J. Animal Sci, 1996, vol. 74, supplement 1, p. 113.*
Cong et al Journal of Biological Chemistry, (1998) vol. 278, p. 660-668.*
Casas et al (J. Animal Sciences (2006) vol. 84, pp. 520-525).*
www.canlii.org/ca/sta/c-46/sec2.html.*
Cong et al (Journal of Biological Chemistry (1998) vol. 273, pp. 660-661.*
N.E. Cockett et al., "Rapid Communication: A *Taq*1 Restriction Fragment Length Polymorphism in the Bovine Calpastatin Gene," J. Anim. Sci. 1995, 73 :3790.
S.F. O'Connoer et al., "Genetic Effects on Beef Tenderness in Bos *indicus* Composite and Bos *taurus* Cattle," J. Anim. Sci. 1997, 75: 1822-1830.
D.M. Wulf et al., "Genetic Influences on Beef Longissimus Palatability in Charolais- and Limousin-Sired Steers and Heifers," J. Anim. Sci. 1996, 74: 2394-2405.
Chung, H. Y., et al., "Genetic Variants Detected by PCR-RFLP in Intron 6 of the Bovine Calpastatin Gene". *Animal Genetics* (Feb., 2001), vol. 32, No. 1, p. 53.
Palmer, B. R., et al., "Single Nucleotide Polymorphisms in an Intron of the Bovine Calpastatine Gene". *Animal Biotechnology* (2000), vol. 11, No. 1, pp. 63-67.
Palmer, B. R., et al., "A Candidate Gene Approach to Animal Quality Traits". *Proceedings of the New Zealand Society of Animal Production* (1997), vol. 57, pp. 294-296.
Green, R. D., et al., "Association of a Taq 1 Capastatin Polymorphism with Postmortem Measures of Beef Tenderness in Bos *Taurus* and Bos *indicus-Bos taurus* Steers and Heifers". *Journal of Animal Science* (1996), vol. 74, No. Suppl. 1:111.
Lonergan, S. M., et al., "Relationship of Restriction Fragment Length Polymorphisms (RFLP) in the Bovine Calpastatin Gene to Muscle Calpastatin Activities and Meat Tenderness". *Journal of Animal Science* (1995), vol. 73, No. Suppl. 1:62.
Lonergan, S. M., "Relationship of Restriction Fragment Length Polymorphisms (RFLP) at the Bovine Calpastatin Locus to Calpastatin Activity and Meat Tenderness". *Journal of Animal Sciences* (Dec., 1995), vol. 73, No. 12, pp. 3608-3612.
Chung, H. Y., et al., "A DNA Polymorphism of the Bovine Calpastatin Gene Detected by SSCP". *Animal Genetics* (Feb. 1999), vol. 30, No. 1, p. 80.

* cited by examiner

*Primary Examiner*—Juliet C Switzer
*Assistant Examiner*—Steven C Pohnert
(74) *Attorney, Agent, or Firm*—Sughrue Mion, PLLC

(57) ABSTRACT

A method for assessing the tenderness of meat from an animal, comprising the step of testing the animal for the presence or absence of a genetic marker selected from the group consisting of:

(1) an allele of the gene encoding calpastatin (CAST) associated with peak-force variation or genetic variation located other than in the CAST gene which shows allelic association with the CAST allele; and
(2) an allele of the gene encoding lysyl oxidase (LOX) associated with instron compression of the semitendinosis muscle or genetic variation located other than in the LOX gene which shows allelic association with the LOX allele.

10 Claims, 12 Drawing Sheets

DNA MARKERS FOR MEAT TENDERNESS

TECHNICAL FIELD

The present invention is concerned with genetic markers for meat tenderness in animals, and with methods and oligonucleotide probes for assessing meat tenderness in said animals, and a kit for this purpose. The invention is useful for the selection of animals which show desirable traits in meat tenderness either for breeding or to select animals destined to be slaughtered for food.

BACKGROUND ART

Meat tenderness is an important issue for consumers, and one which can influence demand sufficiently for an especially tender meat to command a premium price in the marketplace. The physiological change in muscle structure during the post-mortem period is complex but clearly seems to be at least one factor in meat tenderness. The calpain/calpastatin system is an endogenous, calcium-dependent proteinase system, theorised to initiate in vivo muscle protein degradation. Calpastatin appears to inhibit calpain activity and therefore may be assumed to have a role in meat tenderness through the regulation of postmortem proteolysis. In particular, calpain is response for the breakdown of myofibril protein, which is closely related to meat tenderness.

It might therefore be suspected that calpastatin activity will be related to meat tenderness. Indeed, an increase in postmortem calpastatin activity has been correlated to reduced meat tenderness. Nevertheless, despite such observations, no clear link between the CAST gene, which encodes calpastatin, and meat tenderness has been established.

For example, Lonergan et al. (1995) undertook a restriction fragment length polymorphism analysis at CAST and failed to find an association with either calpastatin activity or tenderness in cross bred offspring of sires from eight breeds. Chung et al. (1999) measured calpastatin activity, Warner-Bratzler Shear Force and myofibril fragmentation index in forty-seven purebred Angus bulls. However, they concluded that "PCR single-strand conformation polymorphism analysis of the calpastatin gene was not useful for prediction of calpastatin activity, myofibril fragmentation index or meat tenderness".

It is long known that one of the actions of lysyl oxidase (LOX) is to initiate crosslink formation at an early stage in collagen fibrillogenesis (e.g., Cronlund et al., 1985). The action of lysyl oxidase is intensively studied with hundreds of publications on a variety of aspects of its importance in cancer (Giampuzzi et al., 2001), the vasculature (Nellaiappan et al.) and other tissue and organ systems.

Variation at the gene itself has not been associated with differences in beef tenderness although LOX has always been seen as a strong candidate on biochemical grounds for a gene contributing to the collagen component of tenderness. Analysis of genetic linkage has implicated the genomic region that includes LOX in linkage analysis of family variation in adhesion and instron compression of the semitendinosis muscle (STADH and STIC; Drinkwater et al., 1999). However, LOX itself has not been associated with these measures of tenderness through the study of population associations.

Meat tenderness is a complicated trait because there are many sources of variation that affect postmortem meat tenderisation. Some of these are non-genetic effects such as the age of the beast, the nature of its feed, degree of stress prior to slaughter, carcass chilling, postmortem ageing time and cooking and testing methods. It has been suggested (e.g. Koohmaraie (1994)) that approximately 30% of the variation in tenderness in meat can be explained by additive gene effects within a single breed, and that approximately 70% of the variation is explained by environmental and non-additive gene effects. In the Lonergan study the cattle were slaughtered at just over 1 year of age (430 days), the sample contained only 83 animals of random peak-force values, and the sample consisted entirely of crosses between various taurine breeds. Likewise, in the Chung study purebred Angus bulls only 280 days of age were used. In addition, in neither study were the animales selected for extreme peak-force values, and it therefore seems that environmental and non-fixed genetic effects may have contributed to the failure to identify any genetic linkage between the CAST gene and meat tenderness.

SUMMARY OF THE INVENTION

Through using a protocol designed to reduce the influence of fixed genetic and environmental effects, the present inventor was unexpectedly able to show allelic association between the CAST and LOX genes and meat tenderness. In general terms, therefore, the present invention is concerned with genetic markers for meat tenderness in animals killed for meat which are polymorphisms of the CAST and LOX genes or polymorphisms which show allelic association therewith.

Accordingly, in a first aspect of the present invention there is provided a method for assessing the tenderness of meat from an animal, comprising the step of testing the animal for the presence or absence of a genetic marker selected from the group consisting of:
(1) an allele of the gene encoding calpastatin (CAST) associated with peak-force variation or genetic variation located other than in the CAST gene which shows allelic association with the CAST allele; and
(2) an allele of the gene encoding lysyl oxidase (LOX) associated with variation in instron compression of the semitendinosis muscle or genetic variation located other than in the LOX gene which shows allelic association with the LOX allele.

Preferably, the allele tested for is located in the 3' UTR of CAST, and is typically CAST3 D/E allele 1, having the following partial DNA sequence:

```
catttggaaaacgatgcctcacgtgttcttcagtgttctgatttctcat         (SEQ ID NO:1)

gacccctttcctcttGgacttgtgggactgtgtttgatgtttccctgggttgttgttt ataagtcagtcataaAatactgtgcattgggcacatgtctcctcttgagctgctaatc gtaga,
```

CAST3 D/E allele 2, having the following partial DNA sequence:

```
catttggaaaacgatgcctcacgtgttcttcagtgttctgatttctcat          (SEQ ID NO:2)
gaccccttcctcttAgacttgtgggactgtgtttgatgtttccctgggttgttgttt
ataagtcagtcataaAatactgtgcattgggcacatgtctcctcttgagctgctaatc
gtaga
``` or CAST3 D/E allele 3, having the following partial DNA sequence:

```
catttggaaaacgatgcctcacgtgttcttcagtgttctgatttctcat          (SEQ ID NO:3)
gaccccttcctcttAgacttgtgggactgtgtttgatgtttccctgggttgttgttt
ataagtcagtcataaTatactgtgcattgggcacatgtctcctcttgagctgctaatc
gtaga.
```

Reduced meat toughness is selected for by rejecting animals with the "11" and "12" genotypes and accepting animals with the "22" or "23" genotypes. In the sequences given above, the allelic difference is highlighted with a capital letter. These three alleles in the D/E DNA fragment are due to two SNP (single nucleotide polymorphisms). The first SNP is at base 2655 of Genbank sequence L14450, which is the same as base 2959 of Genbank sequence AF159246; it is a G to A change so that allele 1 has G and alleles 2 and 3 have A. The second SNP is an A to T change 58 base pairs 3' to the first SNP. Since only three alleles have been noted for this region, with 2 SNPS, it implies that there is complete linkage disequillibrium between allele 2 and allele 3, and allele 3 may have evolved from allele 2. This is expected since they are 58 base pairs apart. For predictive purposes, a test of the second SNP which gives a result of allele 3 is equivalent to a test of the first SNP giving a result of allele 2. This is consistent with the peak force values of animals that are '23' heterozygotes, all of whom have low peak force values. While not wishing to be bound by theory, it is believed that these polymorphisms are linked to a mutation in or near the calpastatin gene (perhaps in the promoter or an intron) which results in reduced calpastatin expression or activity.

A further polymorphism has been identified in the 5' UTR of the CAST gene and other polymorphisms which exhibit allelic association with the polymorphism of the 3' UTR, and therefore also act as genetic markers for the tenderness characteristics described above, may also be present at least within the genomic DNA embracing the coding region of the CAST gene and the 5' UTR and 3' UTR regions of that gene. In addition, where there has been a recent reduction in population size for a species, particular haplotypes of individuals will be relatively over-represented. If insufficient time has elapsed to cause allelic association to decay, there will be linkage disequilibrium even for alleles which are far apart.

Livestock species such as cattle have been domesticated from a relatively small pool of wild ancestors in recent times, and therefore in these species allelic association is found between alleles that may be remote physically. Thus, it may be expected that regions of genetic variation that are outside the CAST gene will also show allelic association with the polymorphisms in the CAST gene described above, and therefore will be suitable genetic markers for the characteristic of peak-force variation. Hence, these polymorphisms may also be used to assess meat tenderness.

In particular the CAST5 microsatellite polymorphism (Nonneman et al, 1999) has been found to be useful as a genetic marker for meat tenderness. Of the more common alleles, alleles 7 and 9 have been found to be associated with low peak-force ad allele 3 to be associated with high peak-force.

Therefore, the invention encompasses, in preferred embodiments, the further step of testing for the presence or absence of one or more additional genetic markers such as alleles of the gene encoding calpastatin associated with peak-force variation, in particular, with testing for the presence or absence of CAST5 allele 7 or 9 and/or the presence or absence of CAST5 allele 3. The most favorable results when the presence of CAST D/E allele 2 has been established is to have CAST5 allele 7 or allele 9 present also, whereas the benefits of the presence of CAST D/E allele 2 are to some degree counteracted if the animal also possesses CAST5 allele 3.

The LOX polymorphism has also been shown to be a genetic marker for meat tenderness, and allele 1 or allele 2 may be tested for. Just as for the CAST gene, allelic association may be exhibited to alleles located outside the LOX gene.

The LOX polymorphism has the following partial sequence in which the A-T variant causes the SSCP with allele 1 equal to base T and allele 2 equal to base A:

```
TTATCACTGATGTCAAACCTGGAAACTATATTCTCAAGGTAGAGAACTTT         (SEQ ID NO:4)
GAACATATACCCATAATGTATTTCAATTGTGACTCAGTGGGCTTATTCTC
TGGAGTCAAATGTTAAATATTCATGGTCCTGCAAACAATTATACATCTTC
```

-continued

```
TAGAACTACTT(C/T)TAAACCAACCTAGATATATT(A/T)AAAAAATTC

TTATTTGAAAGAACTTTATGGAAAAAGATCCAGCCTCCTTCAAAAACTCC

AGAGTTGAAACACATGCCTAACTTACACCCTCTTCCTTGCCTGATTTAGT

TGAATTATGCTGTCTCTATTTTAGCCTCCATTCTGGAAAGAGGAAAAAAA

TTAACCAGTAAACACTGCTGATGAAATCTGAAACACAGATGATGTTTGTT

TTGCCTAGGTCAGTGTGAATCCCAGCTATTTGGTGCC.
```

According to a second aspect of the present invention, there is provided a genetic marker for meat tenderness in an animal which is a polymorphic form of the CAST gene, being the CAST3 D/E polymorphism or the LOX polymorphism.

According to a third aspect of the present invention there is provided an isolated DNA molecule comprising the nucleotide sequence set forth in SEQ ID NO:1, SEQ ID NO:2 or SEQ ID NO:3.

According to a fourth aspect of the present invention there is provided an isolated DNA molecule consisting of the nucleotide sequence set forth in SEQ ID NO:1, SEQ ID NO:2 or SEQ ID NO:3.

According to a fifth aspect of the present invention there is provided a method for selecting an animal likely to yield meat of improved tenderness, comprising the steps of:
(1) testing the animal for the presence of an allele of the gene encoding calpastatin (CAST) associated with low peak-force or genetic variation located other than in the CAST gene which shows allelic association with the CAST allele and/or for the presence of an allele of the LOX gene associated with the low instron compression of the semitendinosis muscle or genetic variation located other than in the LOX gene which shows allelic association with the LOX allele; and
(2) selecting animals which have the CAST and/or LOX allele and/or genetic variation in allelic association therewith.

Advantageously, in order to assess the tenderness of meat from an animal and/or select an animal likely to yield meat of improved tenderness testing may comprise the steps of:
(1) obtaining a biological sample from the animal;
(2) extracting DNA from the sample;
(3) amplifying DNA from the CAST or LOX gene and/or from regions of genetic variation which show allelic association to polymorphisms of the relevant one of the CAST or LOX gene; and
(4) identifying the allele present in the amplified DNA.

Typically the allele identified in step (4) is one of CAST3 D/E allele 1, CAST3 D/E allele 2 and CAST3 D/E allele 3 described above and/or the CAST5 alleles described above.

Preferably the biological sample is blood, but other biological samples from which DNA can be amplified may be used. For example, hair root samples, cheek scrapings, skin samples and the like may be used.

Typically amplification is performed using the polymerase chain reaction (PCR), but other DNA amplification methods such as the ligase chain reaction are well known in the art, and may alternatively be used.

Preferably the alleles are identified by polyacrylamide gel electrophoresis techniques such as SSCP, or by other techniques well known to the person skilled in the art such as RFLP analysis.

In a sixth aspect the invention provides an oligonucleotide probe for amplification of a genetic marker associated with peak-force variation, said genetic marker being either an allele of the gene encoding calpastatin (CAST) or genetic variation located other than in the CAST gene which shows allelic association with said allele.

Typically the probe is selected from the group consisting of:

```
castd    5' cat ttg gaa aac gat gcc tca c 3'
         (SEQ ID NO:5)

caste    5' tct acg att agc agc tca aga gga g 3'
         (SEQ ID NO:6)

CAST5U1  5'-GTAAAGCCGCACAAAACACACCCAGG-3'
         (SEQ ID NO:7)

CAST5D1  5'-GTTTCTGGACCCTCTGGATGAGGAAGCGG-3'.
         (SEQ ID NO:8)
```

In view of the designation of the primers as CASTD and CASTE, the amplified fragment of the CAST gene is referred to from time to time as the CAST D/E fragment and the polymorphism as the CAST D/E polymorphism.

According to a seventh aspect of the present invention there is provided an oligonucleotide probe for amplification of a genetic marker associated with variation in instron compression of the semitendinosis muscle, the genetic marker being either an allele of the gene encoding lysyl oxidase (LOX) or genetic variation located other than in the LOX gene which shows allelic association with said allele.

Typically the oligonucleotide probe is an oligonucleotide probe selected from the group consisting of:

```
LOX K5:  5' tat cac tga tgt caa acc tg 3'
         (SEQ ID NO:9)

LOX K6:  5' act cag gca cca aat agc tg 3'.
         (SEQ ID NO:10)
```

According to an eighth aspect of the present invention there is provided a kit for use in assessing the tenderness of meat from an animal and/or selecting an animal likely to yield meat of improved tenderness, comprising oligonucleotide probes for amplification of at least one genetic marker for meat tenderness, said genetic marker being either an allele of the gene encoding calpastatin (CAST) or genetic variation located other than in the CAST gene which shows allelic association with said allele, or an allele of the LOX gene associated with low instron compression of the semitendinosis muscle or genetic variation located other than in the LOX gene which shows allelic association with the LOX allele, and means for amplifying DNA.

The primers used to amplify the DNA are the CASTD and CASTE primers and/or the CAST5U1 and CAST5D1 primers for amplifying the CAST5 polymorphism. However, other primers able to amplify polymorphisms associated with a reduction in toughness in meat are envisaged, whether these be primers which amplify a polymorphism other than the CAST3 D/E polymorphism or CAST5 polymorphism, or other primers able to amplify the CAST3 D/E fragment of CAST5 polymorphism.

The methods of the invention may be used both for the selection of breeding animals and for the selection of unpedigreed animals for entry into feed lots. In the latter case, the methods of the invention allow for animals with unsuitable pedigrees to be excluded from feed lots on the basis that highly tender meat is unlikely to be attained with these animals even after a long feed lot holdings. Alternatively, such measurements may allow for determination of the optimum time to reach maximum meat tenderness. The invention is therefore also concerned with animals when selected by the method of the invention, their progeny and the use of both selected animals and their progeny for breeding, as well as meat from these animals.

The methods of the invention are applicable to animals including but not limited to cattle and other bovids, including water buffalo and bison, to other ungulates, including sheep, goats and deer, and pigs and chickens.

Throughout this specification, the words "comprise", "comprises" and "comprising" are used in a non-exclusive sense, except where the context requires otherwise.

It will be clearly understood that, although a number of prior art publications are referred to herein, this reference does not constitute an admission that any of these documents forms part of the common general knowledge in the art, in Australia or in any other country.

BRIEF DESCRIPTION OF THE DRAWINGS

Preferred embodiments of the present invention will now be described, by way of example only, with reference to the accompanying drawings, in which.

MODES FOR PERFORMING THE INVENTION

EXAMPLE 1

Identification of CAST3 D/E Polymorphism

Cattle were chosen from the DNA Bank of the Cattle and Beef Cooperative Research Centre located in Brisbane, Australia to have as diverse a genetic and phenotypic background as possible. Information stored in the CRC Database was used to select animals. Animals of extremes of peak-force were selected, although animals with peak-force measures above 12 were excluded since they might have confounded peak-force measurements. In essence, the procedure was to select cattle in each contemporary group which were of phenotypic extreme measures, to ensure that no sire was represented by a cluster of offspring, that all markets and finishing regimes were included in each extreme, so that extremes were not biased by being representative of a particular market or finishing regime. A total of 169 samples were obtained (Table 1) for the first sample. A second sample of 77 animals (Table 6) were analysed as a check to determine whether the same allelic association could be observed in another sample.

These DNA samples were genotyped for the CAST (calpastatin) D/E DNA fragment using the primers

```
castd   5' cat ttg gaa aac gat gcc tca c 3'
        (SEQ ID NO:5)

caste   5' tct acg att agc agc tca aga gga g 3'.
        (SEQ ID NO:6)
```

The conditions of the polymerase chain reaction (PCR) are an annealing temperature of 60 Celsius, 2.5 mM Magnesium chloride, and reagent mixes obtained from Biotech International. The DNA fragments were labelled via the incorporation of $^{32}$P dCTP into the fragments during the PCR, and the fragments were visualised by autoradiography using X-Ray film exposed overnight at room temperature. Alleles were scored in numerical order where the fastest migrating allele is number 1.

The genotypes were analysed using generalised linear models (GLM) following the equation peak-force=1+genotypes nested within fixed effects+error implemented via the S-PLUS software. Fixed effects that were considered were breed, finish (Australia, Korea, Japan), contemporary group (cohort), region (pasture v grain, north v south) and the covariate of final weight. The genotypes were nested within region and breed since pure-bred offspring of taurine sires were not pastured in the north. The size of the effects associated with genotype was estimated by the comparison of variances (eg, Andersson-Eklund and Rendel, 1993). To estimate the size of effect associated with genotypic substitution, the same model was fitted without the calpastatin genotypes. Residuals were extracted and compared to the calpastatin genotypes. These were analysed using an analysis of variance to obtain adjusted means for each genotype Plots of raw and residual peak-force values against calpastatin genotypes were constructed.

EXAMPLE 2

Analysis of CAST3 D/E Polymorphism

Figure 1:
FIG. 1 is a photograph of a single strand conformational polymorphism (SSCP) gel which shows genotypes for the CAST3 D/E polymorphism, from left to right, 11, 22, blank, 11, 12, 12, 12, 12, 11, 22.

There are two common alleles (FIG. 1) and at least one rare allele for the CAST D/E polymorphism and both the common alleles are found in all the breeds, although there are clear differences in genotype frequency within the breeds. Zebu breeds have a greater frequency of the '11' genotype (Tables 2 and 7) than taurine breeds in this sample.

Figure 2A:
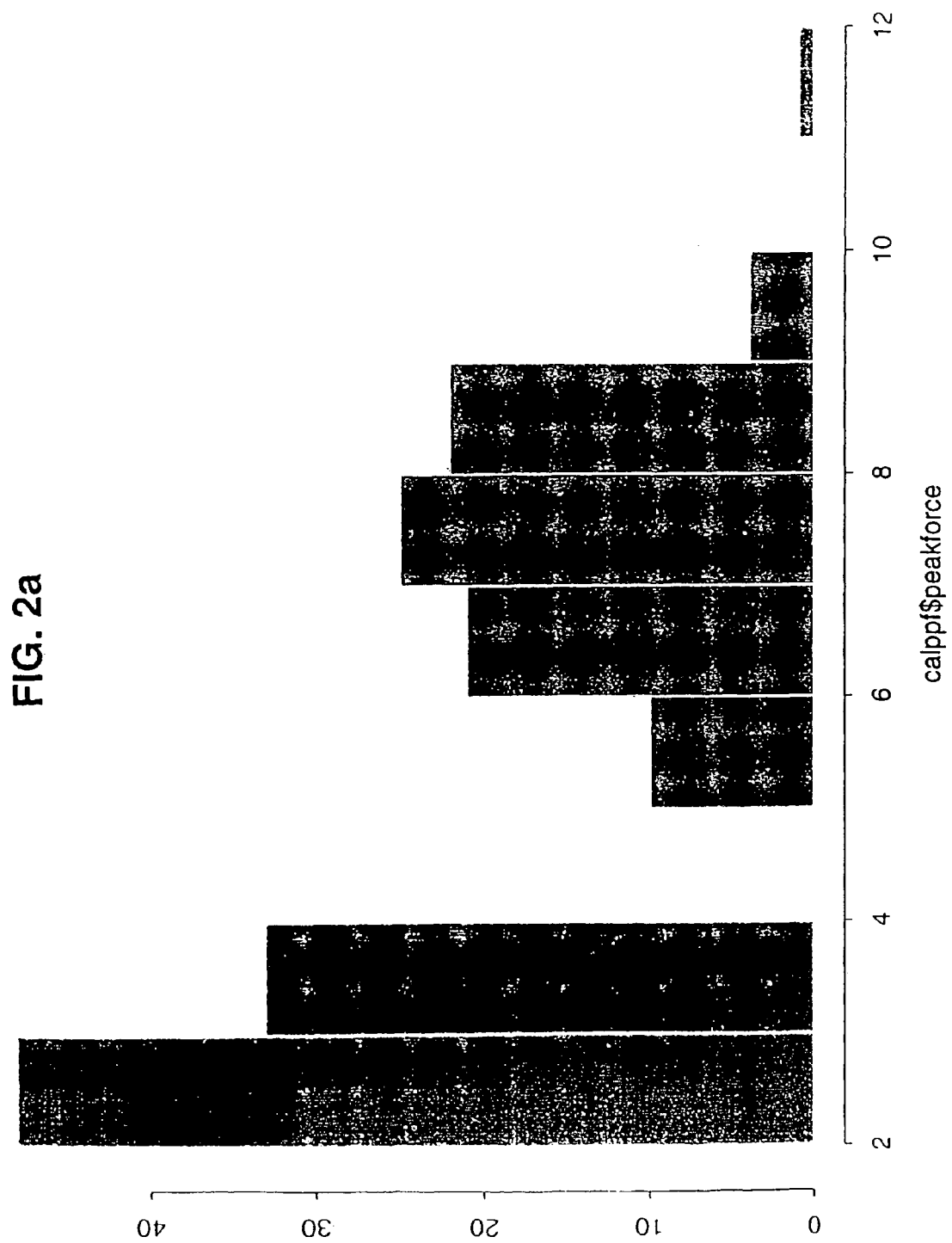
FIGS. 2a & b show the distribution of Warner-Bratzler peak-force measurements in the two samples of 169 and 77 animals respectively. Note that extremes were used so there is no middle to the distribution. It does not imply that the distribution is bi-modal. Note different scales in the figures.
Figure 2B:
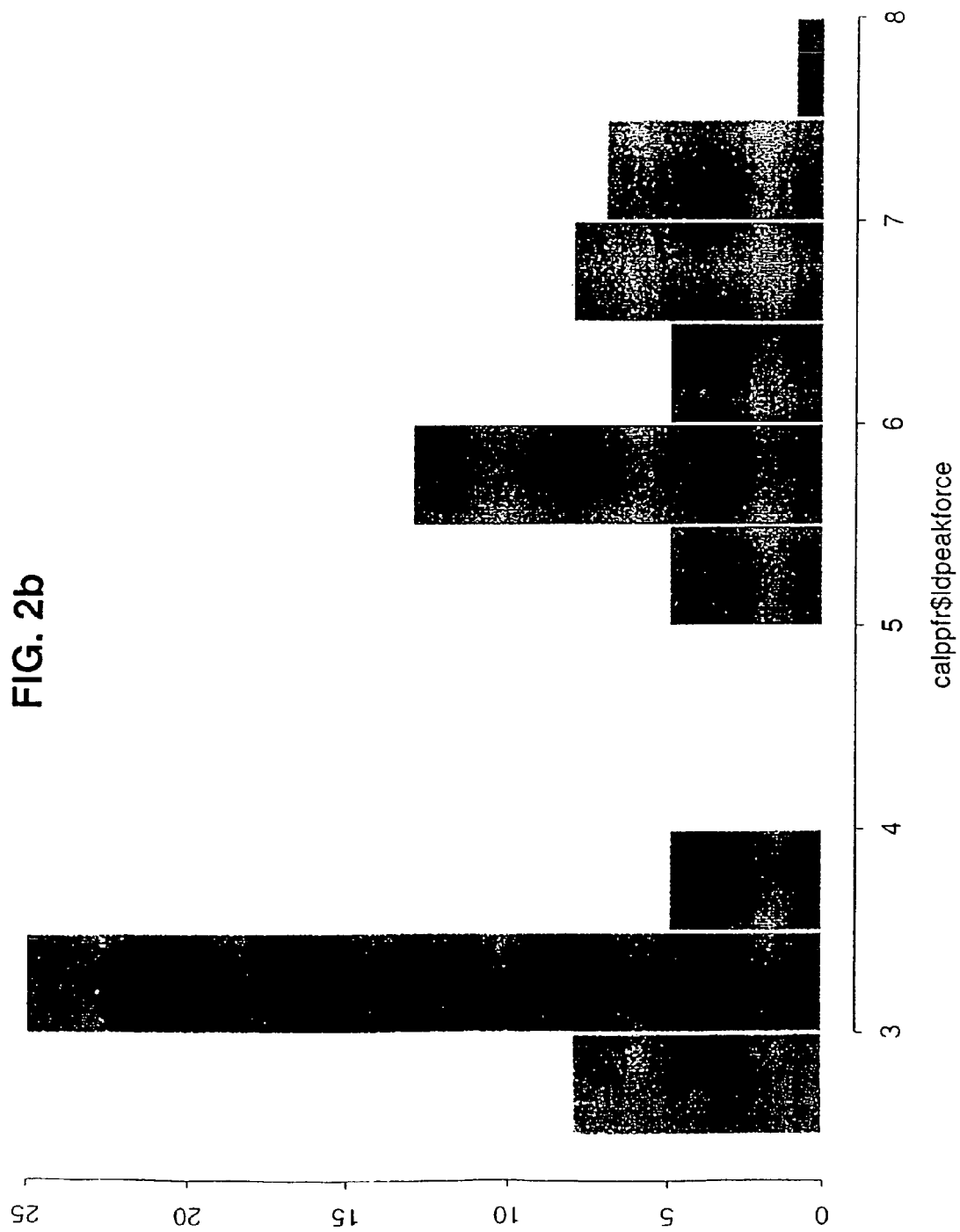
Figure 3A:
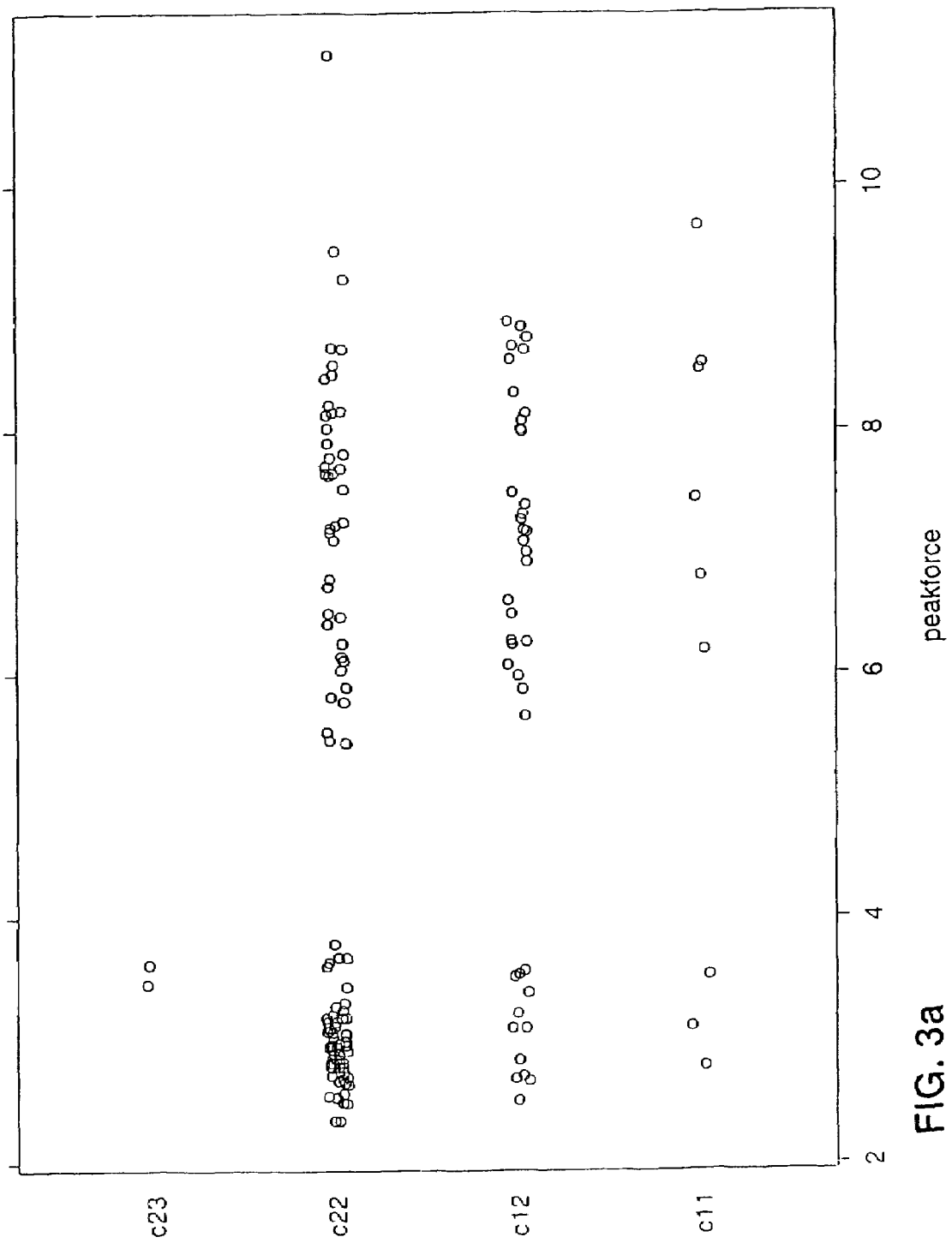
FIGS. 3a & b are a plot of the raw Warner-Bratzler peak-force measurements against the CAST genotypes. Note the gap in the middle due to the use of extremes of the distribution. Note the similarity between the distributions in the two samples.
Figure 3B:
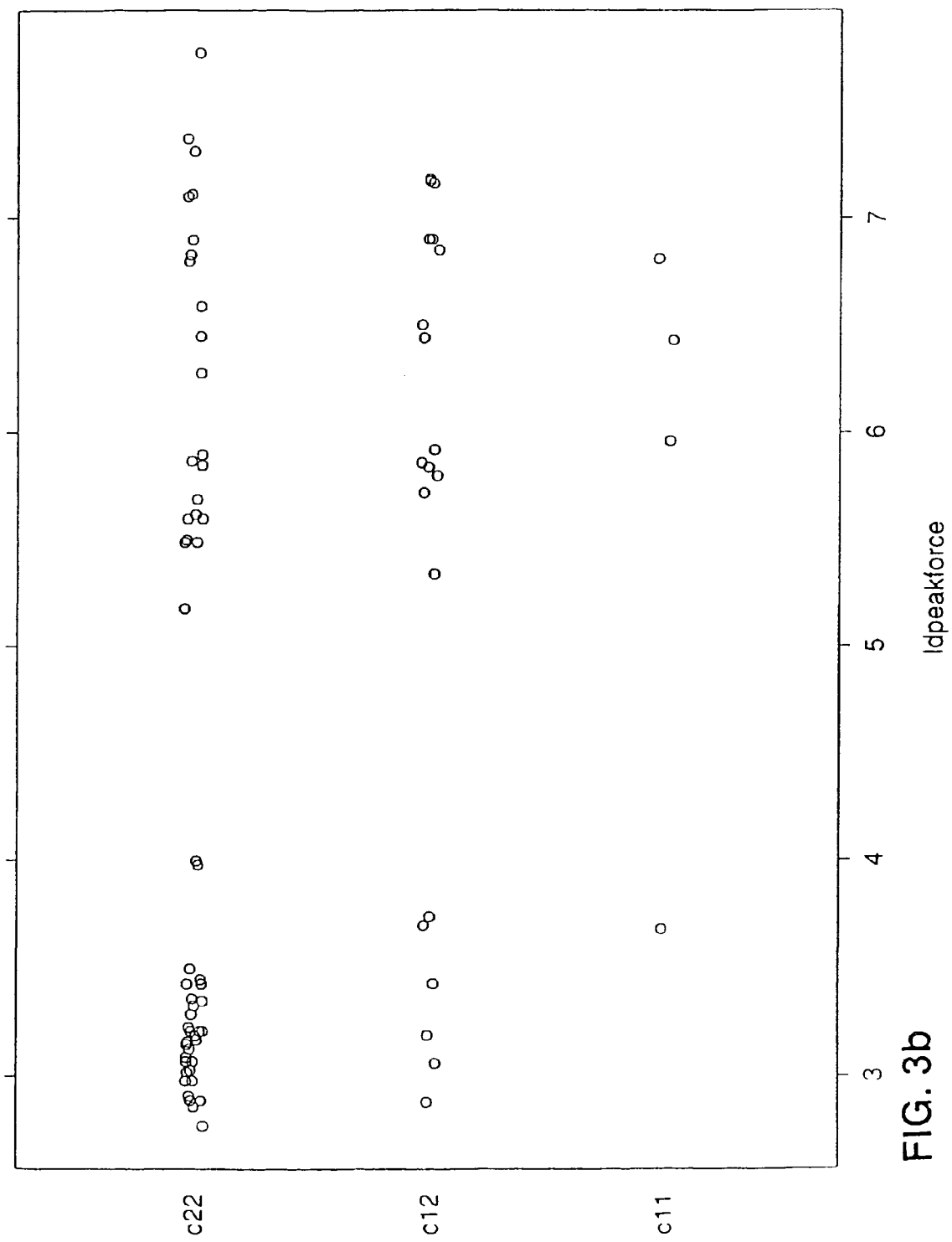

The raw values (FIGS. 2a & 2b) were then plotted against the CAST genotypes (FIGS. 3a & 3b) and these associations are sufficiently strong to show visual associations between peak-force and genotype. The most important genetic effect considered in the literature for CAST, breed or taurine versus zebu, has been carefully matched so that there are animals of high and of low peak-force from each breed in the sample, and breed is not expected to be an explanatory variable here.

The analysis (Table 3) of the CAST genotypes shows strong, confirmatory evidence of effects of the CAST gene or sequences near the CAST gene on peak-force. The analysis shows no effect of breed, but since the sample consists of individuals of high and low peak-force for each breed, this was not unexpected. The size of effect associated with this polymorphism is approximately 7.9 percent of the phenotypic variance estimated as a main effect, and the deviance associated with CAST genotype nested within breed within region is 121.4 (17 df, P=0.001894). An un-nested interaction term between breed and CAST genotype was calculated for this sample, but is was not statistically significant. The GLM of the CAST genotypes (Table 4) against the residual peak force measurements show a statistically significant level of association similar to that of the CAST genotypes considered as a main effect (Table 3) rather than when they are nested within region and breed.

Figure 4:
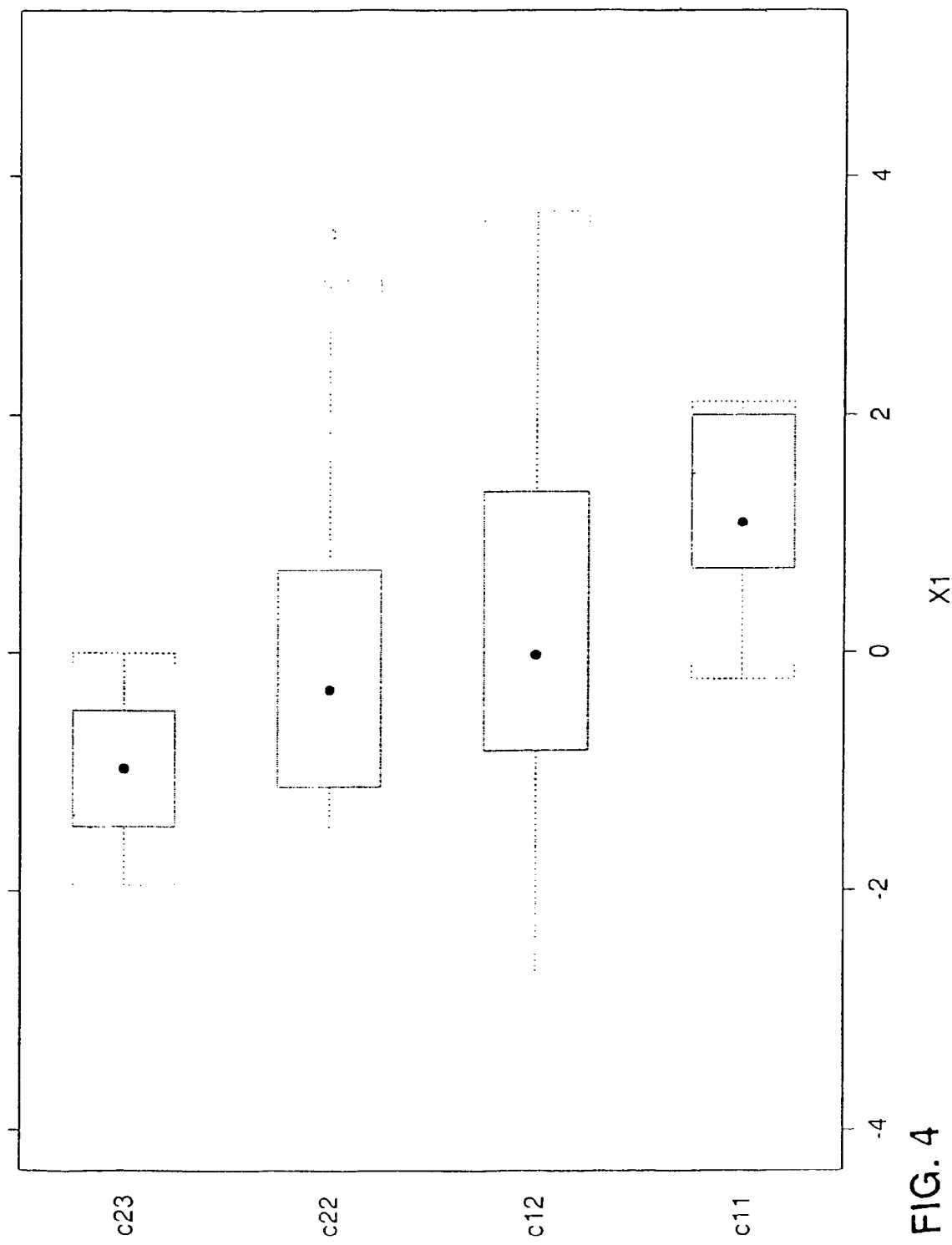
FIG. 4 is a boxplot of the residual Warner-Bratzler peak-force measurements (x1) for each genotype for the first sample. The median quarter and three-quarter percentiles, whiskers and outliers are shown.

A boxplot of genotypes versus the residual peak force measurements (FIG. 4) shows clear differences in distributions and the difference between medians of the '11' and the '22' genotypes are approximately 1.2 kg of adjusted peak force. The adjusted means from the analysis of variance (Table 5) gives a difference of 1.34 kg of peak force between the homozygote genotypes. The overall standard deviation for the residuals is 1.61.

The GLM of the confirmatory sample of 77 animals showed a statistically significant association between CAST genotype and peak force, with the '1' allele associated with higher peak forces. When the full model was calculated, none of the factors were statistically significant, possibly as a result of the relatively small sample size. Terms in the model were dropped one by one using the reduction in AIC as the criterion. All terms except the calpastatin genotypes were dropped (Table 8) in this automatic procedure, and these show a deviance of 17.9 (2 df, P<0.05) explaining 9.5 percent of the phenotypic variance. This is similar to the 8.9 percent found when the CAST genotypes were compared without other factors to peak force in the first sample.

Discussion

The results presented here indicate that genetic variation at the CAST gene is important in explaining variation for Warner-Bratzler peak-force measurements between individuals irrespective of the breed of origin. The sample was chosen to control for the effects of breed and to spread the sample as widely as possible over different sire lines, contemporary groups, feeding and finishing regimes; care was taken to ensure that, as much as possible, individuals in either extreme were from each breed, contemporary group, feeding and finishing system. in this way, systematic effects of these factors on peak-force were controlled so that the effect of the alleles would not be due to inadvertently being carried along by other factors affecting peak-force values. Indeed, there are statistically significant deviations in peak-force due to allelic substitution at this locus even when there is no accounting for the other fixed effects. Inspection of the raw data show frequency differences within breeds for the different genotypes so that the '1' allele is rarer in the extreme with lower peak-force values.

This association between the '1' allele and higher peak force measurements is confirmed in a second smaller sample of extreme animals. These animals are less extreme than those in then first sample, they are the left-over extremes, and they clearly show not only that the calpastatin genotypes are important but that in such a small sample, other factors known to be important are not found to be statistically significant. In a well matched sample such as this it is not of concern, since we attempt to remove the effects of the other factors as much as possible through the choice of samples to analyse.

The size of the homozygote substitution is approximately 1.34 kg of peak force for the LD, equivalent to 0.83 of standard deviation. This value is likely to be overestimated since the extremes of the distribution were used, and a proper estimate will require animals chosen at random from the full distribution of peak force. Nevertheless, this is a useful amount of genetic variance associated with a single marker and it is expected that this marker would be useful in direct DNA marker tests for breeding and feedlot streaming.

The analysis shows no evidence of a breed by genotype interaction on peak-force, which means that there is no evidence that the allele association is different or absent in some breeds. This is interpreted to mean that there is no heterogeneity in the breeds for the association between calpastatin and peak-force.

A positive test for allelic association generally means that the causative mutation is close to the DNA markers. Associations in other studies have indicated that allelic association decays at an extremely rapid rate so that DNA markers even relatively close to a quantitative trait locus will find no evidence of association (e.g., Coleman et al., 1995; Barendse, 1997). This indicates that the causative mutation or mutations are extremely close to the CAST D/E polymorphism.

EXAMPLE 3

Identification of CAST5 Microstatellite Polymorphism

To determine whether other polymorphisms in the CAST gene are associated with tenderness, both of the cattle samples (Tables 1 & 6) were genotyped with the CAST5 microsatellite polymorphism (Nonneman et al, 1999) which was developed from DNA sequence reported earlier (Cong et al., 1998).

The primer sequences to amplify this polymorphism are

```
CAST5U1:  5'-GTAAAGCCGCACAAAACACACCCAGG-3' and
          (SEQ ID NO:7)

Figure 5:
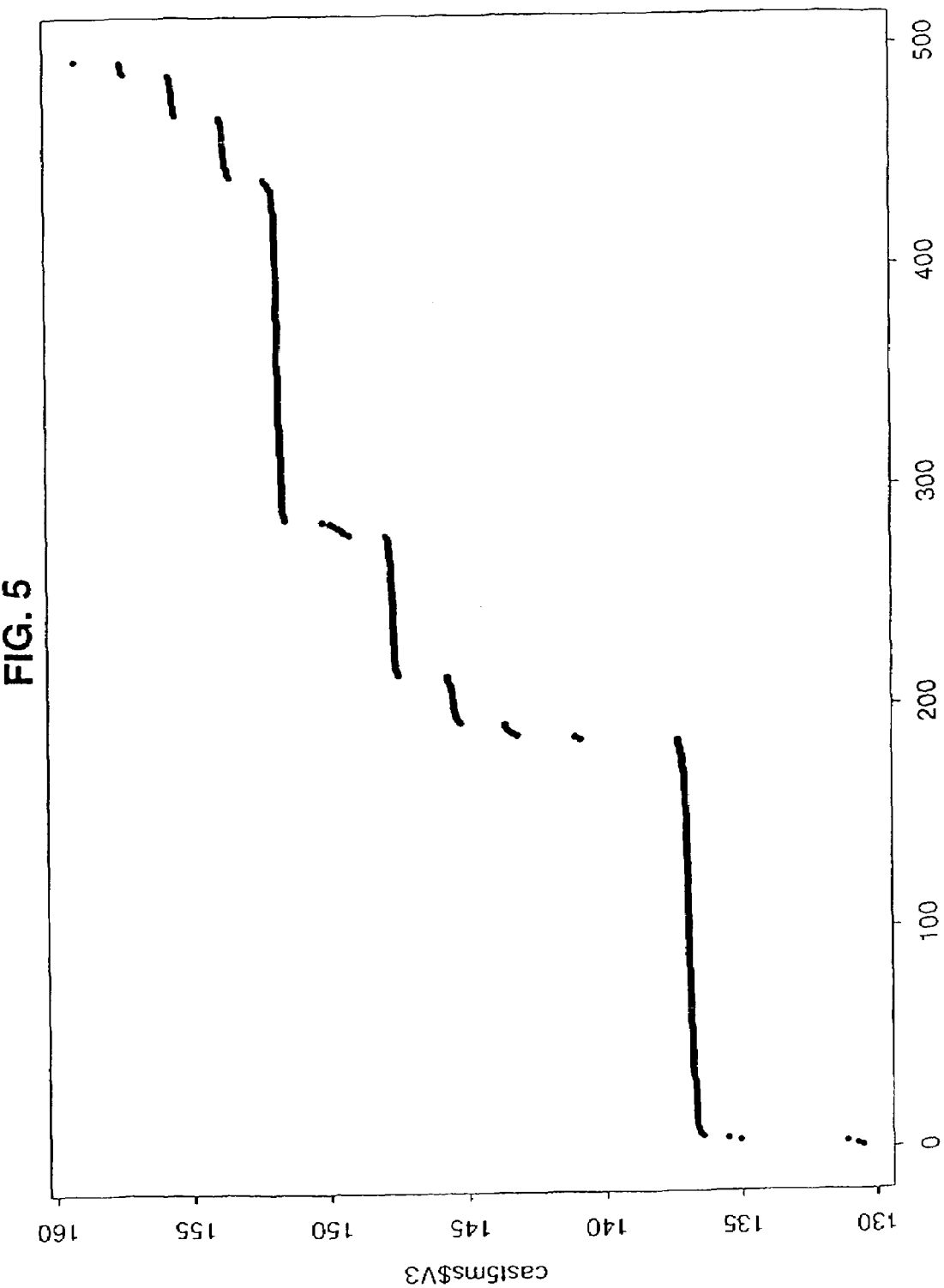
FIG. 5 shows the distribution of DNA fragment sizes for the CAST5 microsatellite. Horizontal axis is the frequency of each allele and the vertical axis is the DNA fragment size. Alleles are labelled in increasing DNA fragment size so allele m1 in this distribution is less than 132 bp, m2<136 bp, m3<138 bp, m4<142 bp, m5<144 bp, m6<146 bp, m7<148 bp, m8<151 bp, m9<153 bp, m10<155 bp, m11<157 bp, m12<159 bp, m13<161 bp. DNA fragments were not found in some of the 2 bp bins, e.g., in the less than 134 bp bin, and these are either extremely rare or non-existent.

CAST5D1:  5'-GTTTCTGGACCCTCTGGATGAGGAAGCGG-3'
          (SEQ ID NO:8)
``` with amplification fragments in the range 130- 159 bp, sizes determined on an ABI 373 DNA sequencer. Alleles and genotypes were assigned based on these size fragments leading to 13 alleles and the distribution of allele sizes is shown in FIG. 5.

Two different sets of analyses were performed. In the first, the genotypes at the CAST3 D/E polymorphism were compared to the CAST5 microsatellite to determine whether there were significant associations between the genotypes, as a consequence of haplotypes existing along the DNA sequence. If CAST5 and CAST3 show significant haplotypes, since they are on either side of the CAST coding sequence, then all polymorphisms for the CAST coding sequence are expected to be in linkage disequillibrium with either or both of these DNA markers. In the second, the CAST5 microsatellite alleles were compared to the LD peak-force measurements to determine whether there was any association between CAST5 and tenderness.

Haplotypes Between CAST5 and CAST3

Since genotypes of parents of these animals were not available haplotypes where determined by analysing animals in which one or both of CAST5 and CAST3 had homozygous genotypes. The frequency of these haplotypes were tabulated (Table 9). These frequencies were tested for heterogenity using a generalised linear model and found to be highly heterogenous (Table 10). This means that each allele at CAST3 D/E is preferentially associated with specific alleles at the CAST5 microsatellite.

Association Between Tenderness and CAST5

Since CAST5 has 13 alleles and hence there are 91 possible genotypes, not all of these genotypes will be seen in a sample of 240 samples, as in this study, so the association was estimated on the alleles. As for the CAST3 D/E DNA marker, the polymorphism was compared to the raw LD peak-force values (Table 11 a), was examined for differences in interactions between breeds (Table 11 b), and was compared to the LD peak-force values after market, cohort, breed and finish effects were accounted for (Table 11 c). In the last of these analyses, CAST5 alleles are nested within finish and breed, as in the analysis of CAST3.

These analyses show that there is no interaction between CAST5 allele frequency and breed on LD peak-force, that the association between CAST5 and the raw LD peak-force values is statistically significant at the threshold P<0.01, but when the CAST5 alleles are nested within breed and finish, the association has a deviation which is 0.1>P>0.05. The lack of interaction between CAST5 and breed in explaining LD peak-force means that any differences in gene frequencies between breeds are not responsible for the association between CAST5 and LD peak-force. The association between CAST5 and LD peak-force in sections a and b of Table 11 indicate that there is some evidence for CAST5 associated with LD peak-force, but a bias might still exist, which is why the factors such as market, cohort, breed and finish are also corrected for. Once those factors are corrected, there is a lack of strength in the association. In the CAST3 D/E analysis, correcting the additional factors improved the evidence for the association, and since the same samples are used, we know in which direction the deviations should go. Thus the lack of strength probably means that the large number of alleles nested within breed and finish, has failed to find an association due to the creation of a large number of categories. Larger numbers of alleles are expected to reduce the strength of associations purely due to the number of categories (of Terwilliger, 1995).

Figure 6:
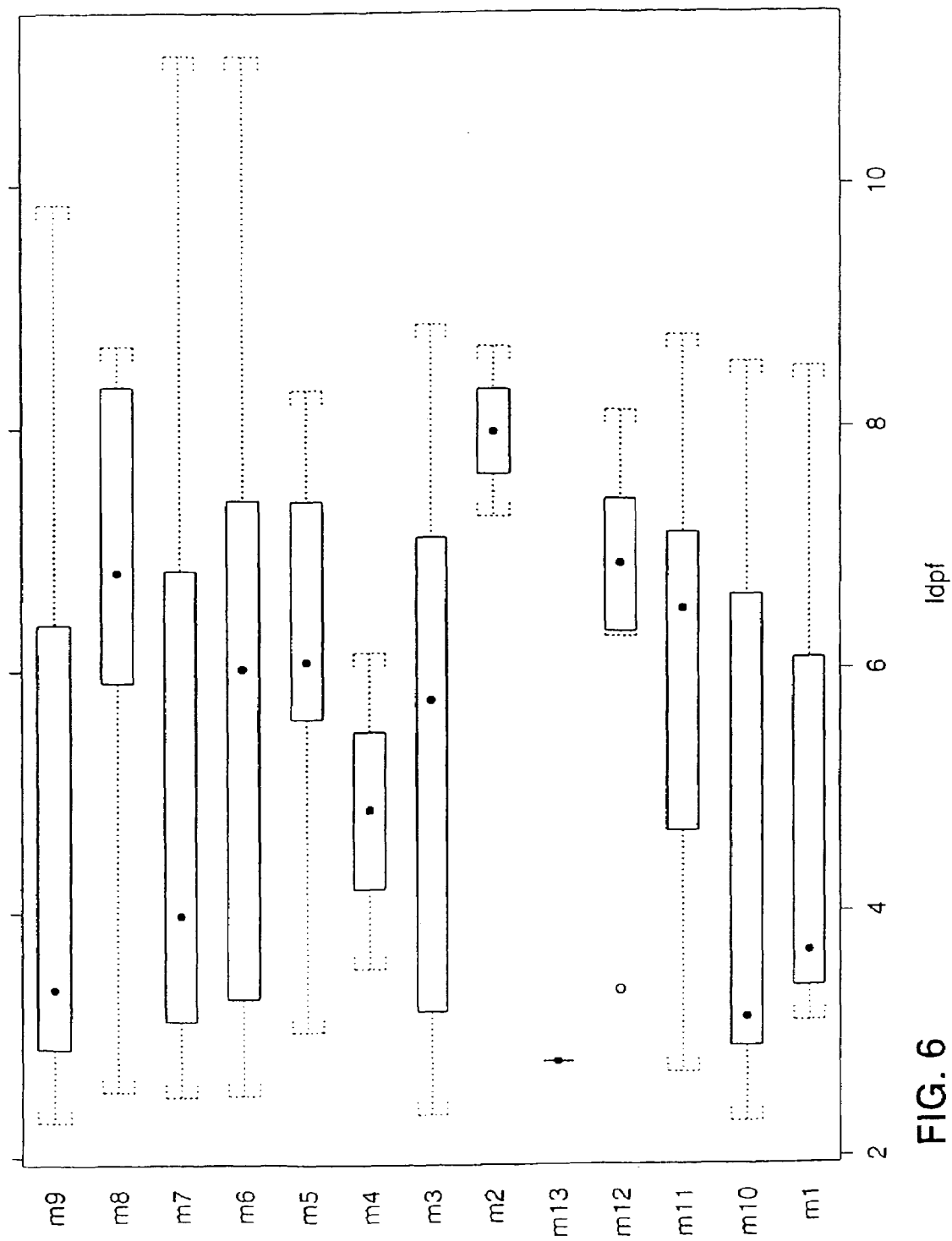
FIG. 6 is a box plot of raw LD peak-force values along the horizontal axis versus CAST5 microsatelite allele identity along the vertical axis. The boxes contain the median value, represented by the dot, a box representing the 25 and 75 percentile and whiskers indicating the expected range for the distributions, with outliers indicated by open circles. Care must be taken in interpreting this figure since there are some alleles that are rare, such as m1, m2 and m13 (see FIG. 5 for the full distribution, so interpretations made on those alleles are not particularly informative. Note particularly that this is a distribution of extreme values, so the median value will swing from a low to a high value if half the samples are high values.

The CAST5 polymorphism can be used in conjunction with the CAST3 D/E polymorphism to predict LD peak-force. For CAST3 D/E the c11 genotype is associated with higher peak force values, the c12 genotype is intermediate and the c22 genotype has the lower peak force values. Secondly, there is linkage disequillibrium between CAST3 D/E and CAST5. By examining the table of haplotypes, looking at the common microsatellite alleles, CAST3 D/E al (allele 1) is most often associated with CAST5 m3 (allele 3) with low abundances for m7 and m9. On the contrary, CAST3 D/E a2 (allele 2) is most often associated with CAST5 m9, with a similar large association to m3 and a lesser but still significant association with m7. Inspection of FIG. 6, a plot of raw LD peak-force values for each CAST5 microsatellite allele, indicates that CAST5 m7 and m9 have lower peak force values while CAST5 m3 has higher peak force values. Since most of the m3 alleles are actually associated with CAST3 D/E a2 and not a1 (108 versus 14), this higher value is not likely to be the effect of CAST D/E a1. Rather it provides a tool to refine the assignment of animals to groups, since animals selected for having CAST3 D/E a2, so that they might have lower peak force values, might still have higher peak force values if they possessed CAST5 m3. They are expected to have a greater likelihood of having lower peak force values if they possessed both CAST3 D/E a2 as well as CAST5 m7 or m9.

EXAMPLE 4

This example shows the testing of a DNA marker in the LOX gene for population associations to STIC and STADH. Repeated statistically significant positive associations were found between genotypes and both STIC and STADH. These indicate that, unusually, the heterozygote may be one of the extreme genotypes suggesting some overdominance. These associations are found in a study of 6 breeds of cattle with a structure to detect linkage disequilibrium and would indicate that the gene LOX either contained or was located near to the genetic factor associated with connective tissue strength.

Materials and Methods

Cattle were chosen from the CRC DNA Bank to have as diverse a genetic and phenotypic background as possible. Two groups of animals were chosen, the first and larger set to test for associations and the second smaller set to confirm the polarity of the associations (cf. Barendse 1997; Barendse et al., 2000). Information stored in the CRC Database was used to select animals. Animals of extremes of instron compression in the semitendinosis muscle were selected. Adhesion measures for these animals were also extracted from the database. In essence, the procedure was to select cattle in each cohort which were of phenotypic extreme measures, to ensure that no sire was represented by a cluster of offspring, that all markets and finishing regimes were included in each extreme, so that extremes were not biased by being representative of a particular market or finishing regime. A total of 253 individuals were selected comprising a first sample of 166 animals and a second sample of 87 animals (Table 11).

The DNA was genotyped for the LOX (Lysyl Oxidase) DNA fragment using the primers LOX K5: 5' tat cac tga tgt caa acc tg 3' (SEQ ID NO:9) and LOX K6: 5' act cag gca cca aat agc tg 3' (SEQ ID NO:10). The conditions of the polymerase chain reaction (PCR) are an annealing temperature of 60 Celsius, 2.5 mM Magnesium chloride, and reagent mixes obtained from Biotech International. The DNA fragments were labeled via the incorporation of $^{32}P$ dCTP into the fragments during the PCR. The fragments were digested with HinfI overnight at 37 Celsius before separation on gels. The fragments were visualised via autoradiography to X-Ray film overnight at room temperature. Alleles were scored in numerical order where the fastest migrating allele is number 1.

The genotypes were analysed using generalised linear models (GLM) following the equation STIC=1+genotypes nested within fixed effects+error implemented via the S-PLUS software. The same model is used for STADH. Fixed effects that were considered were breed, finish (Domestic, Korea, Japan), cohort, region (pasture v grain, north v south) and the covariate of age. Age was included since LOX affects cross-linking of collagen and cross-linking is an age related process, with cross-linking increasing over time. The genotypes were nested within region and breed since pure-bred offspring of taurine sires were not pastured in the north. The size of the effects associated with genotype was estimated by the comparison of variances (eg, Andersson-Eklund and Rendel, 1993). To estimate the size of effect associated with genotypic substitution, the same model was fitted without the LOX genotypes. Residuals were extracted and compared to the LOX genotypes. These were analysed using an analysis of variance to obtain adjusted means for each genotype.

Results

Figure 7:
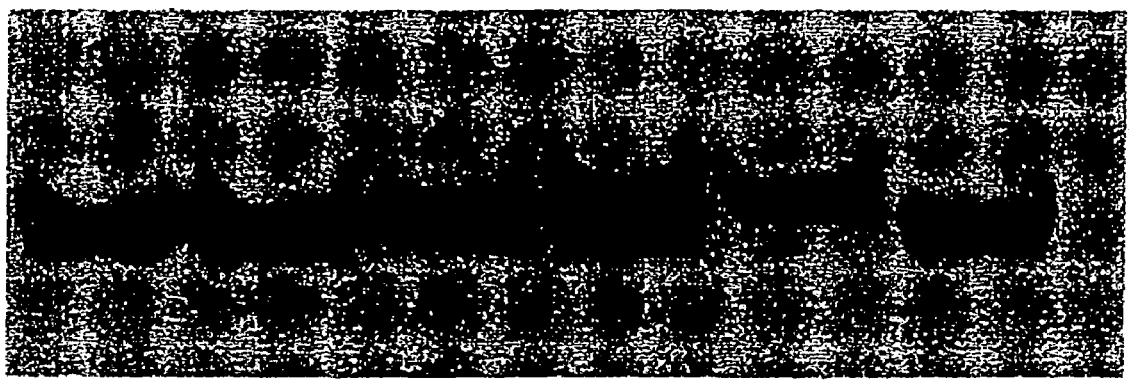
FIG. 7 is a photograph of a single strand conformational polymorphism gel showing the genotypes of LOX from left to right, 11, 11, 12, 12, 22, 11.

There are two alleles (FIG. 7) for the LOX polymorphism and both these alleles are found in all the breeds, although there are clear differences in genotype frequency within the breeds. There is no consistent difference between zebu and taurine breeds in frequency of the genotypes (Table 12). The Hereford breed differs radically in genotype frequencies to all the other breeds in the sample. It has high frequencies of genotype '22' while all other breeds have high frequencies of genotype '11'.

Figure 8:
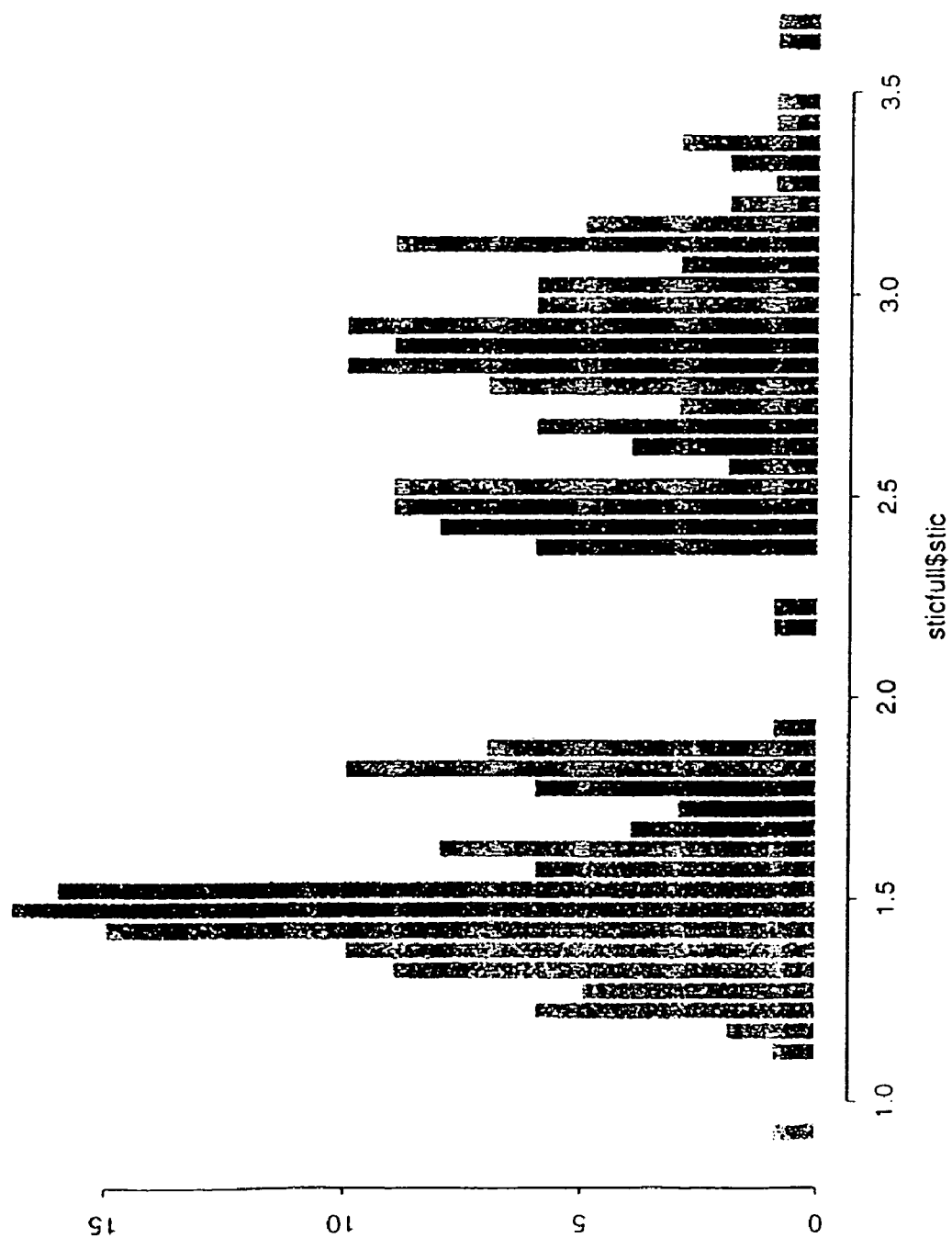
FIG. 8 shows the distribution of instron compression measurements for the two samples of 166 and 87 animals combined. Note that extremes were used so there is no middle to the distribution. It does not imply that the distribution is bi-modal.
Figure 9:
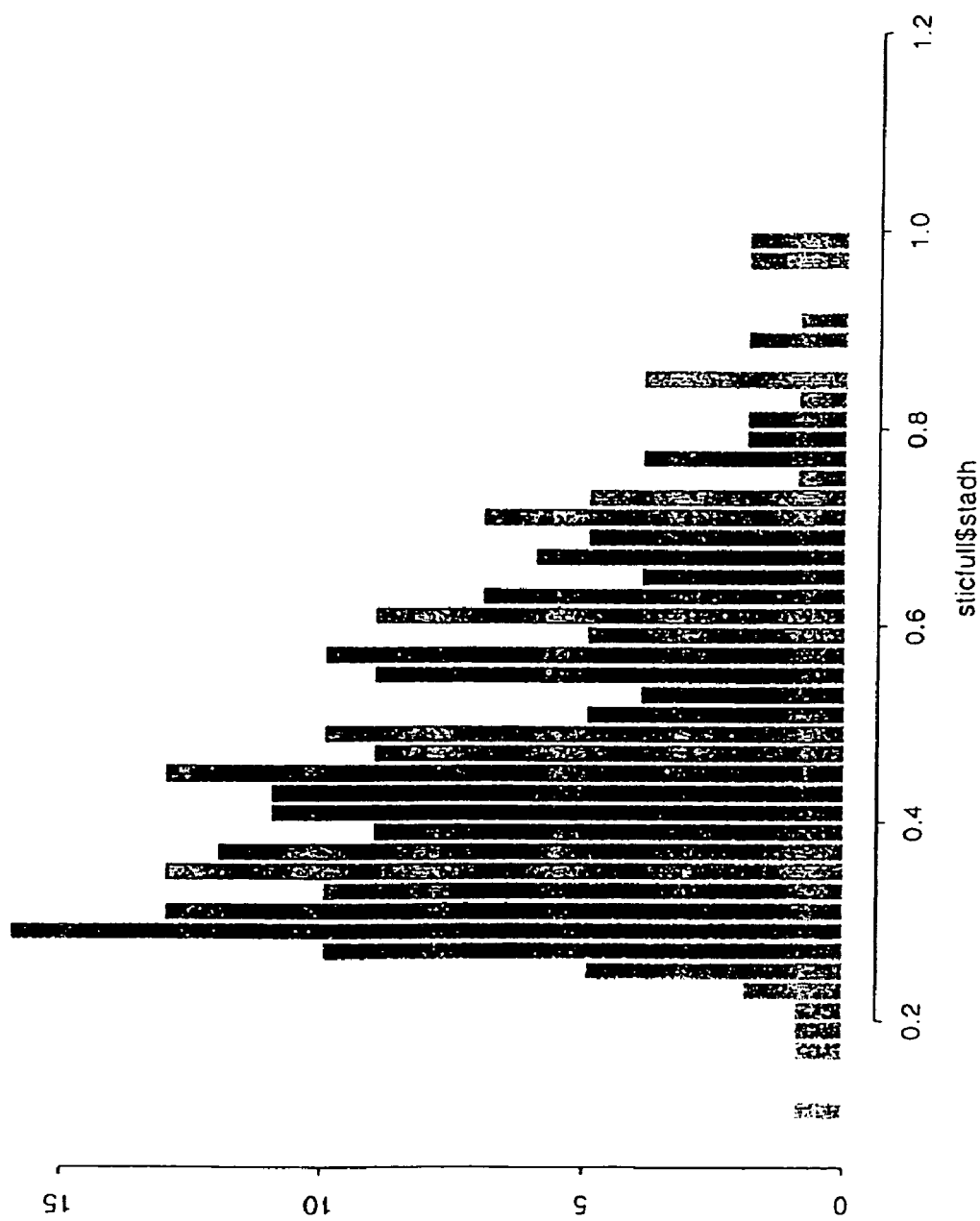
FIG. 9 shows the distribution of adhesion measurements for the two samples of 166 and 87 animals combined. Although the sample was selected for extremes of instron compression, this has not been translated into a series of extreme adhesion measurements.
Figure 10:
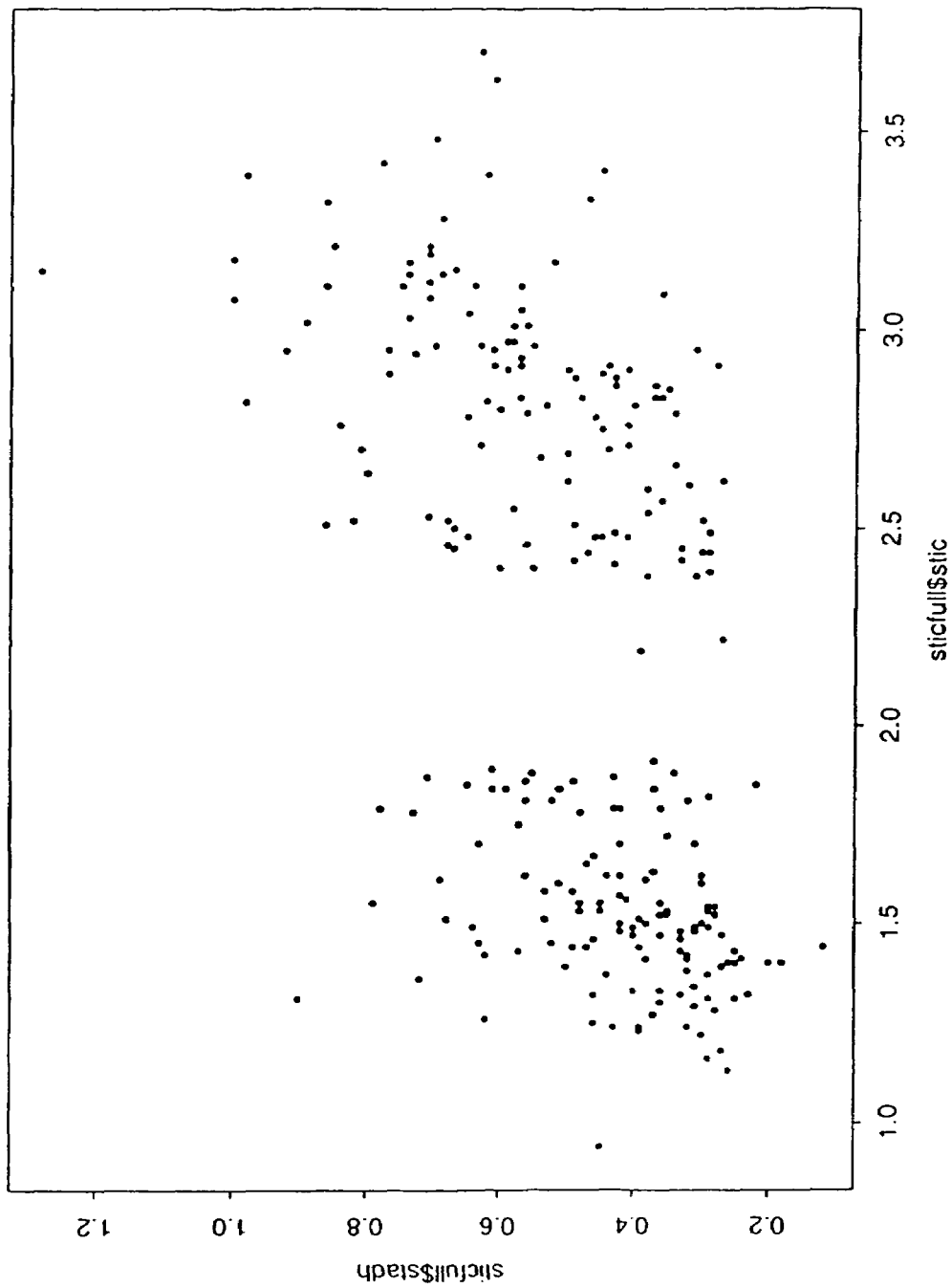
FIG. 10 is a plot of STIC versus STADH for the combined sample. Note the non-uniformity caused by the selected STIC values.

The STIC and STADH values are correlated with R=0.52 (FIGS. 8-10). The plots indicate that while the STIC values show two clear extremes the STADH values have only a long tail and do not show two discrete distributions. This reflects that the sample was selected only on STIC.

The analyses (Tables 13 and 14) of LOX against STIC and STADH show consistent statistically significant associations. The first and the second samples as well as the combined samples of both STIC and STADH show associations to LOX genotypes at P<0.05. The association of LOX appears stronger to STADH than to STIC. The association in the second sample of STADH phenotypes has extremely high statistical significance but this may be due to sampling in small populations and the congruence of extreme phenotypes with particular genotypes. The combined analysis of STADH is less extreme than the second sample but shows confirmatory linkage to LOX (P<0.01).

Nevertheless, it is clear that these are not large genotypic substitution effects and some analyses do not show statistical significance. When the LOX genotypes were compared to residual STIC and STADH, none of these associations was statistically significant, whether by sample or data combined (Table 15). Interestingly, some of the comparisons show that the heterozygotes are of extreme phenotype, opening the possibility of overdominance at this locus. This will need to be confirmed using other polymorphisms at the LOX gene that show larger genotypic substitution effects.

Discussion

Consistent with those earlier analyses, the STADH values show greater association to the DNA marker than the STIC values, even though the samples are extreme for STIC, with STADH values only more dispersed than normal due to the correlation between traits (FIG. 9). STIC was chosen upon which to select extremes rather than STADH. However, both of these measurements evaluate aspects of connective tissue strength, the adhesion measures the force required, in crude terms, to pull a muscle apart, the force applied perpendicular to the fibre bundles, while the instron compression measures how much the muscle can be flattened without being torn or cut. These are not perfectly correlated as can be seen by inspection of the distribution of STIC and STADH values (FIG. 10).

EXAMPLE 5

The association between the marker and STIC was examined in Example 4 using two batches of extreme animals. The results show that there are significant associations between the genotypes of the marker and STIC (instrom compression, P<0.05), and STADH (adhesion, P<0.01). The results suggest that the gene LOX either contains or is located near the genetic factor associated with connective tissue strength.

Because this study was carried out on a relative small population (253) with extreme animals only, the same marker was tested on different populations to see if the association is still valid.

Materials and Methods

In addition to the population, there are two other groups containing animals chosen from the two tails of instron compression (LDIC, 136) and peak force (LDPF, 131) for the LOX gene study. These three extreme groups together with 559 non-extreme individuals form the base for these analyses on the LOX marker. A total of 917 individuals were used for the study (Table 16).

Due to the nature of the populations, the analyses were carried out to the three datasets.

Extreme animals only (389). The extreme animals from LDIC, LDPF and STPF were pooled together.

Non-extreme animals (559).

Combined data (917). The combination of 1 and 2.

Beside the traits STIC, LDPF and LDIC, a range of other traits was also evaluated to see if there is any effect of LOX gene on other meat quality traits (Table 17). The intramuscular fat measurements from LD_FAT % and NIR_FAT % were combined to make a single trait.

The mixed model procedure (MLX) in SAS (version 8.0) was used to run the statistical analyses. The fixed effects in the model include finish group and LOX marker. Sire and contemporary groups are treated as random effects. All these effects were nested within individual breeds. The statistical model used is as follow:

Trait=mean+sire within breed+contemporary group within breed+finish within breed+LOX within breed+Carcass weight.

Contemporary group was defined as the combination of herd of origin, cohort and kill code. The individuals without electrical stimulation were removed from the analysis data. Carcass weight is being used as a covariate to adjust for the age difference.

A full contrast model would be performed if a significant marker-trait association was identified from a mixed model (or GLM) analysis. The purpose of conducting such the test is to further examine the possibility of additive or dominance or overdominance effect among the genotypes of the LOX marker. The full contrast of 3 genotypes (11, 12 and 22) is set up in SAS as follow:

contrast 'Additive Test' lox(bcode) 1 0 −1;
Contrast 'Homozygote1 vs Heterozygote' 1 −1 0
Contrast 'Heterozygote vs Homozygote2' 0 1 −1
contrast 'Dominance Test' lox(bcode) −1 2 −1;
contrast 'Recessive Test' lox(bcode) −1 −1 2;
contrast 'OverDominance Test' lox(bcode) 2 −1 −1;

For the extreme population in which the animals with extreme phenotypes were genotyped, multi-trait logistic regression method (Henshall and Goddard, 1999) was applied to take the potential correlation of traits into account. The method is regression based, but instead of regressing phenotype on genotype, the regression is genotype on phenotype. This replaces the assumption that phenotypes are unselected with the assumption that there was no selection based on genotypes (Henshall and Goddard, 1998). Prior to using logistic regression method, MLX model was used to all data (917 animals) to derive predicted values of individual animals. The predicted phenotype values for the extreme animals after adjusting for significant fixed effects were then used for Logistic regression analyses. The analyses started with single trait logistic regression method and then proceeded to multi-trait logistic regression method.

The genotype frequency distribution of the marker in different populations is shown in Table 18. From the table, it can be seen that the Hereford breed differs remarkably in genotype frequencies to all the other breeds in the populations. In order to investigate the potential effect of skewed genotypes of Hereford breed on the overall results, a set of additional analyses were also pursued to the populations by removing the Hereford individuals from the data sets.

Results and Discussions

Part I. Extreme Animals (Table 19)

Extreme Animals for LDIC

The first test was conducted to the sample containing the selected animals for LDIC (136). The results from the analysis of variance reveal that there was no close association between any genotypes of LOX marker and LDIC. The same conclusion was held to other meat quality traits.

Extreme Animals for LDPF

Like LDIC sample, there was no significant variation detected between the LOX marker and any meat quality trait in the batch animals selected for LDPF. The results are not surprising as the initial QTL for tenderness in CBX experiment was identified in instron compression measurement of Semitendinosus muscles.

Combined Extreme Animal Data

Analysis of Variance. As sire effect was confounded with other effects, it had to be removed from the model and GLM (generalised linear model) was performed. In this case, contemporary group was treated as a fixed effect rather than a random effect. The analysis of variance has shown that out of 21 meat quality traits tested, STIC and LDL had significant results (P<0.05).

Full Contrast Model. The results from full contrast model are given below. For STIC, it can be seen that there was no additive effect between the two homozygous genotypes (11 and 22). However, the highly significant difference between the phenotypes of 11 and 12 obviously contributed to the detection of dominant and overdominant effects. Nothing was remarkable for LDL.

Logistic Regression. After adjusting for the significant fixed effects on all data, logistic regression was applied to STIC. Multi-trait logistic regression model was also fitted to take the potential correlations between ST measurements into account (STIC, STPF and STADH). The results confirm the findings from the other methods. That is, LOX genotypes did have a correlation with STIC. The regression co-efficiency between lox marker and STIC is shown in the output of logistic procedure (below). The allele substitution effect of the lox marker could be derived from the formulae suggested by Henshall and Goddard (1999) based on the total variance of whole data. The multi-trait logistic regression test on STIC, STPF and STADH has shown that both STIC and STPF had significant effects on LOX gene marker. STPF was marginally non-significant in GLM analysis. (Table 20)

Part II. CRC Non-Extreme Animals

The non-extreme animals (559) were genotyped against LOX marker in CRC I and but were not part of the animals involved in marker evaluation Phases III. The mixed model analyses of variance show that beside STIC, the significant marker-trait association was also detected to the intramuscular fat (FAT) and LDPH. However, full contrast test to STIC and FAT has failed to pinpoint the genotype causing the significant results. In the case of LDPH, it seems that 22 genotype had an important role in determining the outcomes. (Table 21)

Part III. Combined Data

When extreme and non-extreme animals were pooled together, the results from mixed model analysis of variance show that again the lox marker was associated with STIC (P<0.05). The significant results were also found in STL, which is the measurement of darkness of carcass meat colour. However in both cases, full contrast model had not be able to identify the significant genotype sources. (Table 22)

Part IV. Removing Hereford Individuals from the Combined Population

In order to test the possible effect of skewed distribution of lox genotypes of Hereford breed, the additional analyses were also performed to the combined data with the removal of Hereford breed. The results indicate that the removal of Hereford animals has changed little to the overall significant results of STIC in the combined population. From the genotype frequency distribution table, it can be seen that the majority of Hereford individuals were from the three extreme populations except one animal from non-extreme CRC population. (Table 23)

The overall results from the investigation of LOX gene effect on meat quality traits have been consistent across three populations (extreme, non-extreme and combined). That is, there is a strong association of LOX gene marker with the instron compression measurement of Semitendinosus muscles (P<0.05). The significant results from other meat quality traits vary from one population to another.

INDUSTRIAL APPLICABILITY

The invention is useful in allowing selection and breeding of animals which yield more tender meat.

TABLE 1

Characteristics of the first Cattle Sample

| | |
|---|---|
| Total: | 169 |
| | 83 high peak force |
| | 86 low peak force |
| Breeds: | 29 Santa Gertrudis |
| | 25 Hereford |
| | 26 Angus |
| | 27 Belmont Red |
| | 31 Brahman |
| | 31 Shorthorn |
| Regions: | 38 Pasture South |
| | 28 Pasture North |
| | 57 Grain South |
| | 41 Grain North |
| Markets: | 72 Korean |
| | 67 Domestic |
| | 25 Japanese |
| Cohorts: | 27 Cohorts |
| | Median: 5 steers per cohort |
| | bottom quartile: 2 steers per cohort |
| | top quartile: 9 steers per cohort |
| Sires: | 112 sires |
| | Median: 1 steer per sire |
| | bottom quartile: 1 steer per sire |
| | top quartile: 2 steers per sire |

TABLE 2

Distribution of CAST genotypes in the breeds in the first sample.

| | Genotype | | | |
|---|---|---|---|---|
| Breed | 11 | 12 | 22 | 23 |
| Angus | 0 | 7 | 19 | 0 |
| Belmont Red | 0 | 8 | 19 | 0 |
| Brahman | 6 | 13 | 10 | 2 |
| Hereford | 0 | 5 | 17 | 0 |
| Santa Gertrudis | 3 | 5 | 19 | 0 |
| Shorthorn | 0 | 4 | 23 | 0 |

TABLE 3

Associations between calpastatin genotypes (castg) and tenderness.

A. Calpastatin by itself
Analysis of Deviance Table
Gaussian model
Response: peakforce
Terms added sequentially (first to last)

| | Df | Deviance Resid. | Df | Resid. Dev | F Value | Pr(F) |
|---|---|---|---|---|---|---|
| NULL | | | 155 | 864.6307 | | |
| castg | 3 | 70.89899 | 152 | 793.7317 | 4.52573 | 0.004536025 |

B. Breed x Calpastatin Interactions
Analysis of Deviance Table
Gaussian model
Response: peakforce
Terms added sequentially (first to last)

| | Df | Deviance Resid. | Df | Resid. Dev | F Value | Pr(F) |
|---|---|---|---|---|---|---|
| NULL | | | 155 | 864.6307 | | |
| finish | 2 | 101.8455 | 153 | 762.7852 | 15.97637 | 0.0000008 |
| cohort | 25 | 273.5882 | 128 | 489.1971 | 3.43339 | 0.0000041 |
| region | 3 | 59.6620 | 125 | 429.5350 | 6.23940 | 0.0005889 |
| breed | 4 | 10.8711 | 121 | 418.6639 | 0.85267 | 0.4948672 |
| castg | 3 | 28.2709 | 118 | 390.3930 | 2.95654 | 0.0355308 |
| breed:castg | 6 | 33.4066 | 112 | 356.9864 | 1.74682 | 0.1166518 |

C. Calpastatin genotypes nested with breed and region
Analysis of Deviance Table
Gaussian model
Response: peakforce
Terms added sequentially (first to last)

| | Df | Deviance Resid. | Df | Resid. Dev | F Value | Pr(F) |
|---|---|---|---|---|---|---|
| NULL | | | 155 | 864.6307 | | |
| finish | 2 | 101.8455 | 153 | 762.7852 | 18.28842 | 0.0000002 |
| cohort | 25 | 273.5882 | 128 | 489.1971 | 3.93027 | 0.0000005 |
| region | 3 | 59.6620 | 125 | 429.5350 | 7.14235 | 0.0002128 |
| breed in region | 7 | 26.8943 | 118 | 402.6408 | 1.37983 | 0.2219802 |
| castg in (region/breed) | 17 | 121.4139 | 101 | 281.2269 | 2.56498 | 0.0018938 |

TABLE 4

Analysis of CAST against residual peakforce measurements (X1).

Analysis of Deviance Table
Gaussian model
Response: X1
Terms added sequentially (first to last)

|       | Df | Deviance Resid. | Df  | Resid. Dev | F Value | Pr(F)      |
|-------|----|-----------------|-----|------------|---------|------------|
| NULL  |    |                 | 154 | 402.3160   |         |            |
| castg | 3  | 21.97947        | 151 | 380.3365   | 2.90874 | 0.03654659 |

Call: glm(formula = X1 castg, data = calppftest, na.action = na.omit)
Coefficients:

| (Intercept) | castg1     | castg2     | castg3     |
|-------------|------------|------------|------------|
| 0.07693593  | −0.4095948 | −0.3102917 | −0.3504961 |

Degrees of Freedom: 155 Total; 151 Residual
Residual Deviance: 380.3365
Model from which residuals were calculated
Analysis of Deviance Table
Gaussian model
Response: peakforce
Terms added sequentially (first to last)

|                 | Df | Deviance Resid. | Df  | Resid. Dev | F Value  | Pr(F)     |
|-----------------|----|-----------------|-----|------------|----------|-----------|
| NULL            |    |                 | 160 | 906.5175   |          |           |
| finish          | 2  | 106.0217        | 158 | 800.4958   | 15.52293 | 0.0000010 |
| cohort          | 26 | 290.8387        | 132 | 509.6571   | 3.27558  | 0.0000057 |
| finlwt          | 1  | 8.0662          | 131 | 501.5908   | 2.36200  | 0.1269337 |
| region          | 3  | 63.9431         | 128 | 437.6478   | 6.24139  | 0.0005629 |
| breed in region | 7  | 24.4323         | 121 | 413.2154   | 1.02206  | 0.4192678 | glm(formula: peakforce = finish + cohort + finlwt + region/breed, data = calppf, na.action = na.omit)

TABLE 5

Analysis of Variance tables between CAST genotypes and residual peak force measures (X1) along with the table of adjusted means associated with each genotype.

Analysis of Variance Table
Response: X1
Terms added sequentially (first to last)

|           | Df  | Sum of Sq | Mean Sq  | F Value | Pr (F)     |
|-----------|-----|-----------|----------|---------|------------|
| castg     | 3   | 21.9795   | 7.326490 | 2.90874 | 0.03654659 |
| Residuals | 151 | 380.3365  | 2.518785 |         |            |

Tables of adjusted means

|    | Grand mean |
|----|------------|
|    | 0.076936   |
| se | 0.318703   |

|    | castg  |        |         |         |
|----|--------|--------|---------|---------|
|    | c11    | c12    | c22     | c23     |
|    | 1.1473 | 0.3281 | −0.1932 | −0.9746 |
| se | 0.5290 | 0.2479 | 0.1564  | 1.1222  |

TABLE 6

Characteristics of the second sample of 77 animals.

| Total: | 77                  |
|--------|---------------------|
|        | 39 high peak force  |
|        | 38 low peak force   |

TABLE 6-continued

Characteristics of the second sample of 77 animals.

| Breeds:  | 11 Belmont Red                      |
|----------|-------------------------------------|
|          | 11 Hereford                         |
|          | 13 Brahman                          |
|          | 13 Shorthorn                        |
|          | 14 Santa Gertrudis                  |
|          | 15 Angus                            |
| Regions: | 24 Pasture South                    |
|          | 12 Pasture North                    |
|          | 21 Grain South                      |
|          | 20 Grain North                      |
| Markets: | 35 Korean                           |
|          | 25 Domestic                         |
|          | 17 Japanese                         |
| Cohorts: | 22 Cohorts                          |
|          | Median: 3 steers per cohort         |
|          | bottom quartile: 2 steers per cohort |
|          | top quartile: 5 steers per cohort   |
| Sires:   | 64 sires                            |
|          | Median: 1 animal per sire           |
|          | bottom quartile: 1 animal per sire  |
|          | top quartile: 1 animal per sire     |

TABLE 7

Distribution of CAST genotypes in the second sample

| | Genotype | | |
|---|---|---|---|
| Breed | 11 | 12 | 22 |
| Angus | 0 | 3 | 12 |
| Belmont Red | 0 | 3 | 8 |
| Brahman | 3 | 7 | 3 |
| Hereford | 0 | 3 | 8 |
| Santa Gertrudis | 1 | 4 | 9 |
| Shorthorn | 0 | 0 | 13 |

TABLE 8

Associations between calpastatin genotypes and LD peak force in the second sample.

Analysis of Deviance Table
Gaussian model
Response: ldpeakforce
Terms added sequentially (first to last)

| | Df | Deviance Resid. | Df | Resid. Dev | F Value | Pr(F) |
|---|---|---|---|---|---|---|
| NULL | | | 76 | 205.9332 | | |
| castg | 2 | 17.90313 | 74 | 188.0300 | 3.522925 | 0.03455689 |

Coefficients:

| (Intercept) | castg1 | castg2 |
|---|---|---|
| 5.227591 | −0.1205 | −0.3719088 |

Degrees of Freedom: 77 Total; 74 Residual
Residual Deviance: 188.03
Single term deletions
Model:
ldpeakforce = lslortwait + buttemp + finish + cohort + region + breed + castg
Final Call:
glm(formula = ldpeakforce castg, data = calppfr, na.action = na.omit)

Coefficients:

| (Intercept) | castg1 | castg2 |
|---|---|---|
| 5.195064 | −0.07055556 | −0.37438 |

Degrees of Freedom: 67 Total; 64 Residual
Residual Deviance: 161.5878

TABLE 9

The amount of each haplotype found between the alleles of the cast5 microsatellite and the cast3 D/E SNP on both cattle samples. Twenty-six haplotypes were found in animals that are homozygous for one or the other locus.

| haplotype | allele cast3 | cast5 | amount |
|---|---|---|---|
| 1 | a1 | m1 | 3 |
| 2 | a1 | m2 | 0 |
| 3 | a1 | m3 | 14 |
| 4 | a1 | m4 | 0 |
| 5 | a1 | m5 | 0 |
| 6 | a1 | m6 | 3 |
| 7 | a1 | m7 | 6 |
| 8 | a1 | m8 | 2 |
| 9 | a1 | m9 | 6 |
| 10 | a1 | m10 | 5 |
| 11 | a1 | m11 | 0 |
| 12 | a1 | m12 | 1 |
| 13 | a1 | m13 | 0 |
| 14 | a2 | m1 | 0 |
| 15 | a2 | m2 | 1 |
| 16 | a2 | m3 | 108 |
| 17 | a2 | m4 | 1 |
| 18 | a2 | m5 | 4 |
| 19 | a2 | m6 | 3 |
| 20 | a2 | m7 | 42 |
| 21 | a2 | m8 | 2 |
| 22 | a2 | m9 | 110 |
| 23 | a2 | m10 | 17 |
| 24 | a2 | m11 | 6 |
| 25 | a2 | m12 | 1 |
| 26 | a2 | m13 | 1 |

Table 10
A heterogeneity test for associations between alleles at CAST5
with alleles at CAST3 D/E.
Analysis of Deviance Table
Poisson model
Response: score

| | Terms added sequentially (first to last) | | | | |
|---|---|---|---|---|---|
| | Df | Deviance Resid. | Df Resid. | Dev | Pr(Chi) |
| NULL | | | 25 | 926.9836 | |
| cast3 | 1 | 220.4994 | 24 | 706.4842 | 0.0000000000 |
| cast5 | 12 | 671.7497 | 12 | 34.7345 | 0.0000000000 |
| cast3:cast5 | 12 | 34.7344 | 0 | 0.0001 | 0.0005161421 |

Table 11
Tests for association between CAST 5 microsatellite and LD peak
force measurements in both cattle samples.
Part A. Calpastatin by itself
Analysis of Deviance Table
Gaussian model
Response: ldpf

| | Terms added sequentially (first to last) | | | | | |
|---|---|---|---|---|---|---|
| | Df | Deviance Resid. | Df Resid. | Dev | F Value | Pr(F) |
| NULL | | | 491 | 2266.640 | | |
| ma111 | 12 | 136.0104 | 479 | 2130.629 | 2.548113 | 0.002843108 |

Part B. Breed by calpastatin interactions
Analysis of Deviance Table
Gaussian model
Response: ld

| | Terms added sequentially (first to last) | | | | | |
|---|---|---|---|---|---|---|
| | Df | Deviance Resid. | Df Resid. | Dev | F Value | Pr(F) |
| NULL | | | 491 | 2266.640 | | |
| market | 2 | 218.4756 | 489 | 2048.164 | 42.35776 | 0.0000000 |
| cohort | 26 | 706.3980 | 463 | 1341.766 | 10.53504 | 0.0000000 |
| finish | 3 | 97.7159 | 460 | 1244.050 | 12.63003 | 0.0000001 |
| breed | 4 | 23.5779 | 456 | 1220.472 | 2.28562 | 0.0594827 |
| cast5 | 12 | 65.7617 | 444 | 1154.711 | 2.12497 | 0.0146070 |
| breed:cast5 | 26 | 76.7170 | 418 | 1077.994 | 1.14414 | 0.2865614 |

Part C. Calpastatin genotypes nested with breed and finish (region)
Analysis of Deviance Table
Gaussian model
Response: ld

| | Terms added sequentially (first to last) | | | | | |
|---|---|---|---|---|---|---|
| | Df | Deviance Resid. | Df Resid. | Dev | F Value | Pr(F) |
| NULL | | | 491 | 2266.640 | | |
| market | 2 | 218.4756 | 489 | 2048.164 | 42.90121 | 0.00000000 |
| cohort | 26 | 706.3980 | 463 | 1341.766 | 10.67020 | 0.00000000 |
| breed | 4 | 30.7280 | 459 | 1311.038 | 3.01697 | 0.01799825 |
| finish % in % reed | 6 | 111.2067 | 453 | 1199.832 | 7.27908 | 0.00000022 |
| cast5 % in % (breed/finish) | 65 | 211.8811 | 388 | 987.950 | 1.28019 | 0.08307834 |

TABLE 11

Characteristics of the Cattle Sample

| | | |
|---|---|---|
| Total: | 166 | 87 |
| high instron compression | 87 | 39 |
| low instron compression | 89 | 38 |
| Breeds: | | |
| Angus | 25 | 12 |
| Belmont Red | 25 | 12 |
| Brahman | 33 | 18 |
| Hereford | 32 | 10 |
| Santa Gertrudis | 26 | 15 |
| Shorthorn | 25 | 17 |
| Regions: | | |
| Pasture South | 47 | 20 |
| Pasture North | 39 | 21 |
| Grain South | 43 | 20 |
| Grain North | 37 | 26 |
| Markets: | | |
| Korean | 81 | 22 |
| Domestic | 47 | 45 |
| Japanese | 38 | 22 |
| Cohorts: | 25 | 14 |
| Median: steers per cohort | 6 | 3 |
| bottom quartile: | 3 | 1 |
| top quartile: | 10 | 11 |
| Sires: | 113 | 62 |
| Median: steers per sire | 1 | 1 |
| bottom quartile: | 1 | 1 |
| top quartile: | 2 | 2 |

TABLE 12

Distribution of LOX genotypes in the breeds in the combined sample.

| | Genotype | | |
|---|---|---|---|
| Breed | 11 | 12 | 22 |
| Angus | 12 | 16 | 5 |
| Belmont Red | 19 | 14 | 2 |
| Brahman | 20 | 21 | 4 |
| Hereford | 1 | 7 | 27 |
| Santa Gertrudis | 18 | 5 | 1 |
| Shorthorn | 23 | 11 | 3 |

TABLE 13

Associations between LOX genotypes (loxg) and STIC.

A. First Sample
Analysis of Deviance Table
Gaussian model
Response: stic
Terms added sequentially (first to last)

| | Df | Deviance Resid. | Df | Resid. Dev | F Value | Pr(F) |
|---|---|---|---|---|---|---|
| NULL | | | 144 | 66.41782 | | |
| market | 2 | 4.68851 | 142 | 61.72932 | 10.11346 | 0.0001124 |
| age | 1 | 0.33061 | 141 | 61.39871 | 1.42631 | 0.2356143 |
| cohort | 23 | 25.50396 | 118 | 35.89474 | 4.78382 | 0.0000000 |
| region | 3 | 2.05111 | 115 | 33.84363 | 2.94960 | 0.0371506 |
| breed % in % region | 8 | 3.73686 | 107 | 30.10677 | 2.01517 | 0.0537829 |
| loxg % in % (region/breed) | 20 | 9.94057 | 87 | 20.16620 | 2.14425 | 0.0081786 |

B. Second Sample
Analysis of Deviance Table
Gaussian model
Response: stic
Terms added sequentially (first to last)

| | Df | Deviance Resid. | Df | Resid. Dev | F Value | Pr(F) |
|---|---|---|---|---|---|---|
| NULL | | | 77 | 36.73118 | | |
| market | 2 | 18.56015 | 75 | 18.17103 | 50.57448 | 0.0000000 |
| age | 1 | 1.22303 | 74 | 16.94800 | 6.66525 | 0.0131586 |
| region | 3 | 0.49228 | 71 | 16.45571 | 0.89428 | 0.4514796 |
| breed % in % region | 9 | 2.26136 | 62 | 14.19435 | 1.36933 | 0.2303598 |
| loxg % in % (region/breed) | 17 | 5.93715 | 45 | 8.25720 | 1.90331 | 0.0433708 |

TABLE 13-continued

Associations between LOX genotypes (loxg) and STIC.

NOTE: cohort could not be fitted as it required a model with more terms than degrees of freedom.
cohort was dropped since that allowed a maximum of other terms to be fitted.

C. Combined Sample
Analysis of Deviance Table
Gaussian model
Response: stic
Terms added sequentially (first to last)

|  | Df | Deviance Resid. | Df | Resid. Dev | F Value | Pr(F) |
|---|---|---|---|---|---|---|
| NULL |  |  | 222 | 105.0131 |  |  |
| market | 2 | 9.28932 | 220 | 95.7238 | 14.63402 | 0.0000015 |
| age | 1 | 0.66404 | 219 | 95.0598 | 2.09221 | 0.1500079 |
| cohort | 23 | 28.46167 | 196 | 66.5981 | 3.89890 | 0.0000002 |
| region | 3 | 0.97412 | 193 | 65.6240 | 1.02306 | 0.3840448 |
| breed % in % region | 9 | 2.08684 | 184 | 63.5372 | 0.73056 | 0.6804229 |
| loxg % in % (region/breed) | 24 | 12.75507 | 160 | 50.7821 | 1.67448 | 0.0327546 |

TABLE 14

Associations between LOX genotypes (loxg) and STADH.

A. First Sample
Analysis of Deviance Table
Gaussian model
Response: stadh
Terms added sequentially (first to last)

|  | Df | Deviance Resid. | Df | Resid. Dev | F Value | Pr(F) |
|---|---|---|---|---|---|---|
| NULL |  |  | 139 | 4.118160 |  |  |
| market | 2 | 0.045611 | 137 | 4.072549 | 1.63665 | 0.2008490 |
| age | 1 | 1.030876 | 136 | 3.041674 | 73.98193 | 0.0000000 |
| cohort | 23 | 1.131428 | 113 | 1.910246 | 3.53035 | 0.0000129 |
| region | 3 | 0.053546 | 110 | 1.856699 | 1.28094 | 0.2863452 |
| breed % in % region | 8 | 0.192061 | 102 | 1.664639 | 1.72293 | 0.1050769 |
| loxg % in % (region/breed) | 19 | 0.508104 | 83 | 1.156535 | 1.91919 | 0.0229812 |

B. Second Sample
Analysis of Deviance Table
Gaussian model
Response: stadh
Terms added sequentially (first to last)

|  | Df | Deviance Resid. | Df | Resid. Dev | F Value | Pr(F) |
|---|---|---|---|---|---|---|
| NULL |  |  | 76 | 3.362345 |  |  |
| market | 2 | 0.560443 | 74 | 2.801903 | 25.18352 | 0.0000000513 |
| age | 1 | 0.486387 | 73 | 2.315516 | 43.71164 | 0.0000000425 |
| region | 3 | 0.390962 | 70 | 1.924554 | 11.71193 | 0.0000090738 |
| breed % in % region | 9 | 0.413632 | 61 | 1.510922 | 4.13035 | 0.0006637134 |
| loxg % in % (region/breed) | 17 | 1.021326 | 44 | 0.489595 | 5.39922 | 0.0000032684 |

C. Combined Sample
Analysis of Deviance Table
Gaussian model
Response: stadh
Terms added sequentially (first to last)

|  | Df | Deviance Resid. | Df | Resid. Dev | F Value | Pr(F) |
|---|---|---|---|---|---|---|
| NULL |  |  | 216 | 7.480742 |  |  |
| market | 2 | 0.268508 | 214 | 7.212234 | 7.78709 | 0.0005990 |
| age | 1 | 1.252352 | 213 | 5.959882 | 72.63985 | 0.0000000 |
| cohort | 23 | 2.111912 | 190 | 3.847971 | 5.32594 | 0.0000000 |
| region | 3 | 0.065737 | 187 | 3.782233 | 1.27098 | 0.2863505 |
| breed % in % region | 9 | 0.325818 | 178 | 3.456415 | 2.09982 | 0.0326124 |
| loxg % in % (region/breed) | 23 | 0.784128 | 155 | 2.672287 | 1.97746 | 0.0079540 |

TABLE 15

Estimated sizes of effects of genotype substitutions at LOX on instron compression and adhesion of the semitendinosus muscle.

Response: stic.resid

| | | | |
|---|---|---|---|
| Grand-mean | 0.027133 | se | 0.053648 |
| Loxg | 111 | 112 | 122 |
| | 0.03958 | −0.02321 | 0.06503 |
| se | 0.07654 | 0.07897 | 0.11751 |

Response: sticbox3.resid

| | | | |
|---|---|---|---|
| Grand-mean | −0.012888 | se | 0.039137 |
| Loxg | 111 | 112 | 122 |
| | 0.033317 | −0.058769 | −0.013213 |
| se | 0.055916 | 0.058431 | 0.085115 |

Response: sticfull.resid

| | | | |
|---|---|---|---|
| Grand-mean | −0.012888 | se | 0.039137 |
| loxg | 111 | 112 | 122 |
| | 0.033317 | −0.058769 | −0.013213 |
| se | 0.055916 | 0.058431 | 0.085115 |

Response: sticadh.resid

| | | | |
|---|---|---|---|
| Grand-mean | 0.002521 | se | 0.010321 |
| Loxg | 111 | 112 | 122 |
| | −0.001426 | −0.002304 | 0.011292 |
| se | 0.014860 | 0.015390 | 0.022384 |

Response: sticbox3adh.resid

| | | | |
|---|---|---|---|
| Grand-mean | 0.004308 | se | 0.012879 |
| loxg | 111 | 112 | 122 |
| | −0.003154 | −0.007446 | 0.023524 |
| se | 0.018594 | 0.018891 | 0.028111 |

Response: sticfulladh.resid

| | | | |
|---|---|---|---|
| Grand-mean | 0.0037399 | se | 0.0092835 |
| loxg | 111 | 112 | 122 |
| | −0.009303 | −0.005244 | 0.025767 |
| se | 0.013379 | 0.013763 | 0.020180 |

TABLE 16

Information on the data sets

| Effect | Class | LDIC | LDPF | Combined Extreme | Non-extreme | Combined |
|---|---|---|---|---|---|---|
| Total | | 136 | 131 | 398 | 543 | 916 |
| Sires | | 96 | 96 | 171 | 61 | 227 |
| Cohorts | | 24 | 24 | 26 | 10 | 30 |
| Breeds | Angus | 19 | 22 | 62 | 134 | 196 |
| | Belmont Red | 23 | 25 | 66 | 140 | 200 |
| | Brahman | 24 | 27 | 76 | 73 | 142 |
| | Hereford | 27 | 14 | 67 | 1 | 68 |
| | Santa Gertrudis | 25 | 24 | 73 | 195 | 257 |
| | Shorthorn | 18 | 19 | 53 | 0 | 53 |
| Regions | Pasture South | 27 | 27 | 92 | 93 | 185 |
| | Pasture North | 24 | 25 | 78 | 144 | 212 |
| | Grain South | 54 | 41 | 125 | 168 | 291 |
| | Grain North | 31 | 38 | 102 | 138 | 228 |
| Markets | Domestic | 47 | 51 | 130 | 240 | 361 |
| | Korean | 61 | 58 | 189 | 201 | 376 |
| | Japaness | 28 | 22 | 78 | 102 | 179 |

TABLE 17

Meat quality traits tested for LOX gene marker

| Code | Trait |
|---|---|
| LD_Fat % | Intramuscular Fat percentage (Soxhylet Method) |
| LD_IC | Longissimus dorsi Instrom compression |
| LD_IY | Longissimus dorsi initial yield (Nth kills only) |
| LD_LOSS | Longissimus dorsi cooking loss % |
| LD_PF | Longissimus dorsi Peak Force - must use "Stim" also |
| LD_PF-IY | Longissimus dorsi Peak Force - initial yield (Nth) |
| LD_a | Longissimus dorsi a* colour |
| LD_b | Longissimus dorsi b* colour |
| LD_1 | Longissimus dorsi L* colour |
| LD_pH | Longissimus dorsi ultimate pH |
| NIR_Fat % | Intramuscular Fat percentage (NIR method) |
| ST_AdhRS | Semitendinosus Shorthose adhesion |
| ST_IC | Semitendinosus Instrom compression |
| ST_IY | Semitendinosus initial yield (Nth kills only) |
| ST_LOSS | Semitendinosus cooking loss % |
| ST_PF | Semitendinosus Peak Force |
| ST_PF-IY | Semitendinosus Peak Force - initial yield (Nth) |
| ST_a | Semitendinosus a* colour |
| ST_b | Semitendinosus b* colour |
| ST_1 | Semitendinosus L* colour |
| ST_pH | Semitendinosus ultimate pH |
| TenderQ | Tenderness Quality as measured by PF (× 100) |

TABLE 18

Distribution of LOX genotypes in the breeds in the three datasets

| | Extreme | | | Non-extreme | | | Combined | | |
|---|---|---|---|---|---|---|---|---|---|
| Breed | 11 | 12 | 22 | 11 | 12 | 22 | 11 | 12 | 22 |
| Angus | 21 | 33 | 7 | 38 | 75 | 21 | 59 | 109 | 28 |
| Brahman | 35 | 35 | 6 | 19 | 40 | 14 | 52 | 71 | 19 |
| Belmont Red | 31 | 23 | 12 | 59 | 60 | 21 | 87 | 83 | 30 |
| Hereford | 4 | 17 | 46 | 0 | 1 | 0 | 4 | 18 | 46 |
| Santa Gertrudis | 42 | 29 | 2 | 120 | 62 | 13 | 156 | 86 | 15 |
| Shorthorn | 34 | 18 | 1 | 0 | 0 | 0 | 34 | 18 | 1 |
| Total | 167 | 156 | 74 | 236 | 238 | 69 | 392 | 385 | 139 |

TABLE 19

The GLM Procedure
Dependent Variable: STIC

| Source | DF | Sum of Squares | Mean Square | F Value | Pr > F |
|---|---|---|---|---|---|
| Model | 297 | 90.3108958 | 0.3040771 | 2.54 | <.0001 |
| Error | 97 | 11.5922526 | 0.1195078 | | |
| Corrected Total | 394 | 101.9031484 | | | |

TABLE 19-continued

| | R-Square | Coeff Var | Root MSE | STIC Mean | |
|---|---|---|---|---|---|
| | 0.886242 | 16.41081 | 0.345699 | 2.106532 | |

| Source | DF | Type III SS | Mean Square | F Value | Pr > F |
|---|---|---|---|---|---|
| contemp(Bcode) | 269 | 72.05453149 | 0.26786071 | 2.24 | <.0001 |
| Fingp(Bcode) | 3 | 0.56463473 | 0.18821158 | 1.57 | 0.2004 |
| Stim | 1 | 0.29426415 | 0.29426415 | 2.46 | 0.1199 |
| lox(Bcode) | 12 | 3.23498136 | 0.26958178 | 2.26 | 0.0145 |
| wt | 1 | 0.62547588 | 0.62547588 | 5.23 | 0.0243 |

| Contrast | DF | Contrast SS | Mean Square | F Value | Pr > F |
|---|---|---|---|---|---|
| Additive Test 11-22 | 1 | 0.42074192 | 0.42074192 | 3.52 | 0.0636 |
| 11-12 | 1 | 2.17031475 | 2.17031475 | 18.16 | <.0001 |
| 12-22 | 1 | 0.17567132 | 0.17567132 | 1.47 | 0.2283 |
| Dominance Test | 1 | 0.97536352 | 0.97536352 | 8.16 | 0.0052 |
| Recessive Test | 1 | 0.00964320 | 0.00964320 | 0.08 | 0.7770 |
| OverDominance Test | 1 | 1.58776355 | 1.58776355 | 13.29 | 0.0004 |

| Parameter | Estimate | Standard Error | t Value | Pr > \|t\| |
|---|---|---|---|---|
| Additive Test 11-22 | −0.54698783 | 0.29151964 | −1.88 | 0.0636 |
| 11-12 | −0.93226650 | 0.21876446 | −4.26 | <.0001 |
| 12-22 | 0.38527867 | 0.31777709 | 1.21 | 0.2283 |
| Dominance Test | 1.31754517 | 0.46119045 | 2.86 | 0.0052 |
| Recessive Test | 0.16170916 | 0.56927504 | 0.28 | 0.7770 |
| OverDominance Test | −1.47925433 | 0.40583359 | −3.64 | 0.0004 |

LDL
The GLM Procedure
Dependent Variable: LD1

| Source | DF | Sum of Squares | Mean Square | F Value | Pr > F |
|---|---|---|---|---|---|
| Model | 295 | 4070.356476 | 13.797819 | 1.96 | <.0001 |
| Error | 96 | 675.059834 | 7.031873 | | |
| Corrected Total | 391 | 4745.416310 | | | |

| | R-Square | Coeff Var | Root MSE | LD1 Mean | |
|---|---|---|---|---|---|
| | 0.857745 | 6.920726 | 2.651768 | 38.31633 | |

| Source | DF | Type III SS | Mean Square | F Value | Pr > F |
|---|---|---|---|---|---|
| contemp(Bcode) | 267 | 2628.383772 | 9.844134 | 1.40 | 0.0278 |
| Fingp(Bcode) | 3 | 25.195055 | 8.398352 | 1.19 | 0.3161 |
| Stim | 1 | 0.195851 | 0.195851 | 0.03 | 0.8678 |
| lox(Bcode) | 12 | 160.954945 | 13.412912 | 1.91 | 0.0427 |
| wt | 1 | 5.974613 | 5.974613 | 0.85 | 0.3590 |

| Contrast | DF | Contrast SS | Mean Square | F Value | Pr > F |
|---|---|---|---|---|---|
| Additive Test | 1 | 5.88718974 | 5.88718974 | 0.84 | 0.3625 |
| 11 vs 12 | 1 | 3.08780445 | 3.08780445 | 0.44 | 0.5091 |
| 12 vs 22 | 1 | 1.03256209 | 1.03256209 | 0.15 | 0.7024 |
| Dominance Test | 1 | 0.01778689 | 0.01778689 | 0.00 | 0.9600 |
| Recessive Test | 1 | 3.27515251 | 3.27515251 | 0.47 | 0.4966 |
| OverDominance Test | 1 | 7.23682011 | 7.23682011 | 1.03 | 0.3129 |

| Parameter | Estimate | Standard Error | t Value | Pr > \|t\| |
|---|---|---|---|---|
| Additive Test 11-22 | −2.04608559 | 2.23617248 | −0.91 | 0.3625 |
| 11-12 | −1.11200497 | 1.67809812 | −0.66 | 0.5091 |
| 12-22 | −0.93408062 | 2.43759636 | −0.38 | 0.7024 |
| Dominance Test | 0.17792435 | 3.53769859 | 0.05 | 0.9600 |
| Recessive Test | 2.98016622 | 4.36676923 | 0.68 | 0.4966 |
| OverDominance Test | −3.15809056 | 3.11305081 | −1.01 | 0.3129 |

TABLE 20

Single Trait Logistic Regression
The LOGISTIC Procedure
Model Information

| | |
|---|---|
| Data Set | WORK.EXTRERES |
| Response Variable | lox |
| Number of Response Levels | 3 |
| Number of Observations | 389 |
| Link Function | Logit |
| Optimization Technique | Fisher's scoring |

Response Profile

| Ordered Value | lox | Total Frequency |
|---|---|---|
| 1 | 11 | 165 |
| 2 | 12 | 153 |
| 3 | 22 | 71 |

NOTE: 8 observations were deleted due to missing values for the response or explanatory variables.

The LOGISTIC Procedure
Testing Global Null Hypothesis: BETA = 0

| Test | Chi-Square | DF | Pr > ChiSq |
|---|---|---|---|
| Likelihood Ratio | 5.0720 | 1 | 0.0243 |
| Score | 5.0502 | 1 | 0.0246 |
| Wald | 5.0083 | 1 | 0.0252 |

Analysis of Maximum Likelihood Estimates

| Parameter | DF | Estimate | Standard Error | Chi-Square | Pr > ChiSq |
|---|---|---|---|---|---|
| Intercept | 1 | 0.9245 | 0.5608 | 2.7174 | 0.0993 |
| Intercept2 | 1 | 2.7482 | 0.5777 | 22.6278 | <.0001 |
| sticpred | 1 | −0.5827 | 0.2604 | 5.0083 | 0.0252 |

Odds Ratio Estimates

| Effect | Point Estimate | 95% Wald Confidence Limits | |
|---|---|---|---|
| sticpred | 0.558 | 0.335 | 0.930 |

Multi-trait Logistic Regression
The LOGISTIC Procedure
Testing Global Null Hypothesis: BETA = 0

| Test | Chi-Square | DF | Pr > ChiSq |
|---|---|---|---|
| Likelihood Ratio | 14.7234 | 3 | 0.0021 |
| Score | 14.5859 | 3 | 0.0022 |
| Wald | 13.9424 | 3 | 0.0030 |

Analysis of Maximum Likelihood Estimates

| Parameter | DF | Estimate | Standard Error | Wald Chi-Square | Pr > ChiSq |
|---|---|---|---|---|---|
| Intercept 11 | 1 | −0.9210 | 0.8702 | 1.1202 | 0.2899 |
| Intercept 12 | 1 | 0.9467 | 0.8711 | 1.1813 | 0.2771 |
| sticpred | 1 | −0.8681 | 0.3191 | 7.4014 | 0.0065 |
| stadhpred | 1 | −0.4025 | 0.7724 | 0.2715 | 0.6023 |
| stpfpred | 1 | 0.5689 | 0.1936 | 8.6313 | 0.0033 |

Odds Ratio Estimates

| Effect | Point Estimate | 95% Wald Confidence Limits | |
|---|---|---|---|
| sticpred | 0.420 | 0.225 | 0.785 |
| stadhpred | 0.669 | 0.147 | 3.039 |
| stpfpred | 1.766 | 1.208 | 2.581 |

TABLE 21

The Mixed Procedure
Model Information

| | |
|---|---|
| Data Set | WORK.CRC1 |
| Dependent Variable | STIC |
| Covariance Structure | Variance Components |
| Estimation Method | REML |
| Residual Variance Method | Profile |
| Fixed Effects SE Method | Model-Based |
| Degrees of Freedom Method | Containment |

Covariance Parameter Estimates

| Cov Parm | Estimate | Standard Error | Z Value | Pr Z |
|---|---|---|---|---|
| SireID(Bcode) | 0.002544 | 0.002147 | 1.18 | 0.1181 |
| contemp(Bcode) | 0.008813 | 0.003896 | 2.26 | 0.0118 |
| Residual | 0.07009 | 0.005174 | 13.55 | <.0001 |

Type 3 Tests of Fixed Effects

| Effect | Num DF | Den DF | F Value | Pr > F |
|---|---|---|---|---|
| Fingp(Bcode) | 9 | 317 | 17.50 | <.0001 |
| Stim | 1 | 317 | 1.75 | 0.1870 |
| lox(Bcode) | 8 | 317 | 2.36 | 0.0176 |
| wt | 1 | 317 | 6.45 | 0.0115 |

Estimates

| Label | Estimate | Standard Error | DF | t Value | Pr > |t| |
|---|---|---|---|---|---|
| Additive Test 11-22 | 0.05547 | 0.07813 | 317 | 0.71 | 0.4782 |
| 11-12 | 0.1044 | 0.05660 | 317 | 1.84 | 0.0661 |
| 12-22 | −0.04890 | 0.07013 | 317 | −0.70 | 0.4861 |
| Dominance Test | −0.1533 | 0.1007 | 317 | −1.52 | 0.1289 |
| Recessive Test | −0.00657 | 0.1373 | 317 | −0.05 | 0.9619 |
| OverDominance Test | 0.1598 | 0.1170 | 317 | 1.37 | 0.1730 |

Contrasts

| Label | Num DF | Den DF | F Value | Pr > F |
|---|---|---|---|---|
| Additive Test 11-22 | 1 | 317 | 0.50 | 0.4782 |
| 11-12 | 1 | 317 | 3.40 | 0.0661 |
| 12-22 | 1 | 317 | 0.49 | 0.4861 |
| Dominance Test | 1 | 317 | 2.32 | 0.1289 |
| Recessive Test | 1 | 317 | 0.00 | 0.9619 |
| OverDominance Test | 1 | 317 | 1.87 | 0.1730 |

Instramuscuar Fat
The Mixed Procedure
Model Information

| | |
|---|---|
| Data Set | WORK.CRC1 |
| Dependent Variable | Fat |
| Covariance Structure | Variance Components |
| Estimation Method | REML |
| Residual Variance Method | Profile |
| Fixed Effects SE Method | Model-Based |
| Degrees of Freedom Method | Containment |

Covariance Parameter Estimates

| Cov Parm | Estimate | Standard Error | Z Value | Pr Z |
|---|---|---|---|---|
| SireID(Bcode) | 0.04848 | 0.04510 | 1.07 | 0.1412 |
| contemp(Bcode) | 0.3111 | 0.1060 | 2.93 | 0.0017 |
| Residual | 1.2479 | 0.09791 | 12.75 | <.0001 |

TABLE 21-continued

Type 3 Tests of Fixed Effects

| Effect | Num DF | Den DF | F Value | Pr > F |
|---|---|---|---|---|
| Fingp(Bcode) | 9 | 306 | 7.08 | <.0001 |
| Stim | 1 | 306 | 0.31 | 0.5790 |
| lox(Bcode) | 8 | 306 | 2.00 | 0.0461 |
| wt | 1 | 306 | 74.54 | <.0001 |

Estimates

| Label | Estimate | Standard Error | DF | t Value | Pr > |t| |
|---|---|---|---|---|---|
| Additive Test 11-22 | 0.3765 | 0.3427 | 306 | 1.10 | 0.2728 |
| 11-12 | −0.1207 | 0.2505 | 306 | −0.48 | 0.6304 |
| 12-22 | 0.4972 | 0.3029 | 306 | 1.64 | 0.1018 |
| Dominance Test | 0.6179 | 0.4377 | 306 | 1.41 | 0.1591 |
| Recessive Test | −0.8737 | 0.5964 | 306 | −1.47 | 0.1439 |
| OverDominance Test | 0.2558 | 0.5184 | 306 | 0.49 | 0.6220 |

Contrasts

| Label | Num DF | Den DF | F Value | Pr > F |
|---|---|---|---|---|
| Additive Test 11-22 | 1 | 306 | 1.21 | 0.2728 |
| 11-12 | 1 | 306 | 0.23 | 0.6304 |
| 12-22 | 1 | 306 | 2.69 | 0.1018 |
| Dominance Test | 1 | 306 | 1.99 | 0.1591 |
| Recessive Test | 1 | 306 | 2.15 | 0.1439 |
| OverDominance Test | 1 | 306 | 0.24 | 0.6220 |

LDPH
The Mixed Procedure
Model Information

| | |
|---|---|
| Data Set | WORK.CRC1 |
| Dependent Variable | LDpH |
| Covariance Structure | Variance Components |
| Estimation Method | REML |
| Residual Variance Method | Profile |
| Fixed Effects SE Method | Model-Based |
| Degrees of Freedom Method | Containment |

Covariance Parameter Estimates

| Cov Parm | Estimate | Standard Error | Z Value | Pr Z |
|---|---|---|---|---|
| contemp(Bcode) | 0.002771 | 0.000702 | 3.95 | <.0001 |
| Residual | 0.007878 | 0.000572 | 13.77 | <.0001 |

Type 3 Tests of Fixed Effects

| Effect | Num DF | Den DF | F Value | Pr > F |
|---|---|---|---|---|
| Fingp(Bcode) | 9 | 363 | 3.44 | 0.0004 |
| Stim | 1 | 363 | 1.14 | 0.2854 |
| lox(Bcode) | 8 | 363 | 3.01 | 0.0027 |
| wt | 1 | 363 | 21.61 | <.0001 |

Estimates

| Label | Estimate | Standard Error | DF | t Value | Pr > |t| |
|---|---|---|---|---|---|
| Additive Test 11-22 | −0.1089 | 0.02648 | 363 | −4.11 | <.0001 |
| 11-12 | −0.01502 | 0.01922 | 363 | −0.78 | 0.4351 |
| 12-22 | −0.09393 | 0.02376 | 363 | −3.95 | <.0001 |
| Dominance Test | −0.07891 | 0.03416 | 363 | −2.31 | 0.0215 |
| Recessive Test | 0.2029 | 0.04650 | 363 | 4.36 | <.0001 |
| OverDominance Test | −0.1240 | 0.03971 | 363 | −3.12 | 0.0019 |

The Mixed Procedure
Contrasts

| Label | Num DF | Den DF | F Value | Pr > F |
|---|---|---|---|---|
| Additive Test 11-22 | 1 | 363 | 16.93 | <.0001 |
| 11-12 | 1 | 363 | 0.61 | 0.4351 |
| 12-22 | 1 | 363 | 15.63 | <.0001 |
| Dominance Test | 1 | 363 | 5.34 | 0.0215 |
| Recessive Test | 1 | 363 | 19.04 | <.0001 |
| OverDominance Test | 1 | 363 | 9.75 | 0.0019 |

TABLE 22

STIC
The Mixed Procedure
Covariance Parameter Estimates

| Cov Parm | Estimate | Standard Error | Z Value | Pr Z |
|---|---|---|---|---|
| SireID(Bcode) | 0.006141 | 0.004815 | 1.28 | 0.1011 |
| contemp(Bcode) | 0.05433 | 0.01003 | 5.42 | <.0001 |
| Residual | 0.09190 | 0.006489 | 14.16 | <.0001 |

Type 3 Tests of Fixed Effects

| Effect | Num DF | Den DF | F Value | Pr > F |
|---|---|---|---|---|
| Fingp(Bcode) | 11 | 369 | 9.24 | <.0001 |
| Stim | 2 | 369 | 4.06 | 0.0181 |
| lox(Bcode) | 12 | 369 | 1.90 | 0.0336 |
| wt | 1 | 369 | 9.93 | 0.0018 |

Estimates

| Label | Estimate | Standard Error | DF | t Value | Pr > |t| |
|---|---|---|---|---|---|
| Additive Test 11-22 | 0.06327 | 0.08142 | 369 | 0.78 | 0.4376 |
| 11-12 | 0.07985 | 0.05752 | 369 | 1.39 | 0.1659 |
| 12-22 | −0.01658 | 0.07440 | 369 | −0.22 | 0.8238 |
| Dominance Test | −0.09643 | 0.1052 | 369 | −0.92 | 0.3598 |
| Recessive Test | −0.04669 | 0.1450 | 369 | −0.32 | 0.7476 |
| OverDominance Test | 0.1431 | 0.1198 | 369 | 1.20 | 0.2328 |

Contrasts

| Label | Num DF | Den DF | F Value | Pr > F |
|---|---|---|---|---|
| Additive Test 11-22 | 1 | 369 | 0.60 | 0.4376 |
| 11-12 | 1 | 369 | 1.93 | 0.1659 |
| 12-22 | 1 | 369 | 0.05 | 0.8238 |
| Dominance Test | 1 | 369 | 0.84 | 0.3598 |
| Recessive Test | 1 | 369 | 0.10 | 0.7476 |
| OverDominance Test | 1 | 369 | 1.43 | 0.2328 |

STL
Covariance Parameter Estimates

| Cov Parm | Estimate | Standard Error | Z Value | Pr Z |
|---|---|---|---|---|
| SireID(Bcode) | 0.4389 | 0.3429 | 1.28 | 0.1003 |
| contemp(Bcode) | 3.3608 | 0.7375 | 4.56 | <.0001 |
| Residual | 10.6090 | 0.6789 | 15.63 | <.0001 |

TABLE 22-continued

Type 3 Tests of Fixed Effects

| Effect | Num DF | Den DF | F Value | Pr > F |
|---|---|---|---|---|
| Fingp(Bcode) | 11 | 368 | 16.40 | <.0001 |
| Stim | 2 | 368 | 4.68 | 0.0098 |
| lox(Bcode) | 12 | 368 | 2.18 | 0.0124 |
| wt | 1 | 368 | 8.64 | 0.0035 |

Estimates

| Label | Estimate | Standard Error | DF | t Value | Pr > |t| |
|---|---|---|---|---|---|
| Additive Test 11-22 | −0.7500 | 0.8582 | 368 | −0.87 | 0.3827 |
| 11-12 | −0.6732 | 0.5998 | 368 | −1.12 | 0.2625 |
| 12-22 | −0.07683 | 0.7815 | 368 | −0.10 | 0.9217 |
| Dominance Test | 0.5963 | 1.0975 | 368 | 0.54 | 0.5872 |
| Recessive Test | 0.8268 | 1.5279 | 368 | 0.54 | 0.5887 |
| OverDominance Test | −1.4232 | 1.2576 | 368 | −1.13 | 0.2585 |

Contrasts

| Label | Num DF | Den DF | F Value | Pr > F |
|---|---|---|---|---|
| Additive Test 11-22 | 1 | 368 | 0.76 | 0.3827 |
| 11-12 | 1 | 368 | 1.26 | 0.2625 |
| 12-22 | 1 | 368 | 0.01 | 0.9217 |
| Dominance Test | 1 | 368 | 0.30 | 0.5872 |
| Recessive Test | 1 | 368 | 0.29 | 0.5887 |
| OverDominance Test | 1 | 368 | 1.28 | 0.2585 |

TABLE 23

The Mixed Procedure
Covariance Parameter Estimates

| Cov Parm | Estimate | Standard Error | Z Value | Pr Z |
|---|---|---|---|---|
| SireID(Bcode) | 0.005452 | 0.004008 | 1.36 | 0.0869 |
| contemp(Bcode) | 0.03915 | 0.008774 | 4.46 | <.0001 |
| Residual | 0.09105 | 0.006426 | 14.17 | <.0001 |

Type 3 Tests of Fixed Effects

| Effect | Num DF | Den DF | F Value | Pr > F |
|---|---|---|---|---|
| Fingp(Bcode) | 10 | 368 | 10.46 | <.0001 |
| Stim | 2 | 368 | 5.89 | 0.0030 |
| lox(Bcode) | 10 | 368 | 2.28 | 0.0132 |
| wt | 1 | 368 | 7.14 | 0.0079 |

Estimates

| Label | Estimate | Standard Error | DF | t Value | Pr > |t| |
|---|---|---|---|---|---|
| Additive Test 11-22 | 0.06263 | 0.07965 | 368 | 0.79 | 0.4322 |
| 11-12 | 0.09181 | 0.05618 | 368 | 1.63 | 0.1031 |
| 12-22 | −0.02918 | 0.07277 | 368 | −0.40 | 0.6887 |
| Dominance Test | −0.1210 | 0.1028 | 368 | −1.18 | 0.2398 |
| Recessive Test | −0.03345 | 0.1419 | 368 | −0.24 | 0.8137 |
| OverDominance Test | 0.1544 | 0.1171 | 368 | 1.32 | 0.1879 |

Contrasts

| Label | Num DF | Den DF | F Value | Pr > F |
|---|---|---|---|---|
| Additive Test 11-22 | 1 | 368 | 0.62 | 0.4322 |
| 11-12 | 1 | 368 | 2.67 | 0.1031 |
| 12-22 | 1 | 368 | 0.16 | 0.6887 |
| Dominance Test | 1 | 368 | 1.39 | 0.2398 |
| Recessive Test | 1 | 368 | 0.06 | 0.8137 |
| OverDominance Test | 1 | 368 | 1.74 | 0.1879 |

REFERENCES

The contents of the following documents are incorporated herein by reference:

Andersson-Eklund, L. and Rendel, J. 1993. Linkage between amylase-I locus and a major gene for milk fat content in cattle. Animal Genetics 24, 101-103.

Barendse, W. 1997. Assessing lipid metabolism. Patent application PCT/AU98/00882

W. Barendse and B. Harrison (2001) The analysis of effects on instron compression and adhesion in the semitendinosus muscle of genotypes at the candidate gene Lysyl Oxidase (LOX) in cattle of diverse breeds. CRC commercial-in-confidence report.

Barendse, W., Harrison, B. and Li, Y. 2000. The analysis of effects on peak-force of genotypes at the candidate gene Calpastatin in cattle of diverse breeds. Confidential Report of the Beef Quality CRC.

Chung, H. Y., Davis, M. E. and Hines, H. C. 1999. A DNA polymorphism of the bovine calpastatin gene detected by SSCP analysis. Animal Genetics 30, 80.

Chung, H. Y., Davis, M. E., Hines, H. C. and Wulf, D. M. 1999. Relationship of a PCR-SSSCP at the bovine Calpastatin locus with Calpastatin activity and. Meat Tenderness. Ohioline Bulletin Special Circular 170-99. http://www.ag.ohio-state.edu/~ohioline/sc170/sc170_3.html Coleman, J. B., Cucca, F., Hearne, C. M., Cornall, R. J., Reed, P. W., Ronningen, K. S., Undlien, D. E., Nistico, L., Buzzetti, R., Tosi, R., Pociot, F., Nerup, J., ornelis, F., Barnett, A. H., Bain, .C., and Todd, J. A. 1995. Linkage disequilibrium mapping of a type 1 diabetes susceptibility gene (IDDM7) to chromosome 2q31-q33. Nature Genetics 9, 80-85.

Cronlund, A. L., Smith, B. D., Kagan, H. M. 1985. Binding of lysyl oxidase to fibrils of type I Collagen. Connective Tissue Research 14, 109-119.

Drinkwater, R. D., Harrison, B., Byrne, K., Botero, F. A., Knight, M., Davis, G. P., Lenane, I., Li, Y., Kuipers, R., and Moore, S. S. 1999. Candidate genes for Meat Quality, draft report for the 1998-1999 research program. Cattle and Beef CRC Commercial-In-Confidence Report.

Ekholm, E. C., Ravanti, L., Kahari, V., Paavolainen, P. and Penttinen, R. P. 2000. Expression of extracellular matrix genes; transforming growth factor (TGF)-beta1 and ras in tibial fracture healing of lathyritic rats. Bone 27, 551-557.

Geesink, G. H. and Koohmaraie, M. 1999. Postmortem proteolysis and calpain/calpastatin activity in callipyge and normal lamb biceps femoris during extended postmortem storage. J. Anim. Sci. 77, 1490-1501.

Giampuzzi, M., Botti, G., Cilli, M., Gusmano, R., Borel, A., Sommer, P., Di Donato, A. 2001. Down regulation of lysyl oxidase induced tumorigenic transformation in NRK-49F cells characterized by constitutive activation of Ras proto-oncogene. Journal of Biological Chemistry [epub ahead of print].

J. Henshall and M. Goddard (1999) Multiple-trait mapping of quantitative trait loci after selective genotyping using logistic regression. Genetics 151:885-894.

Y. Li (2000) CRC Molecular Genetics Program Annual Report. CRC commercial-in-confidence report.

Lonergan, S. M., Ernst, C. W., Bishop, M. D., Calkins, C. R., and Koohmaraie, M. 1995. Relationship of restriction fragment length polymorphisms (RFLP) at the bovine calpastatin locus to calpastatin activity and meat tenderness. J.Anim. Sci 73, 3608-3612.

Koohmaraie, M. 1994. Muscle proteinases and meat aging meat Sci. 36:93.

Nellaiappan, K., Risitano, A., Liu, G., Nicklas, G. and Kagan, K. M. 2000. Fully processed lysyl oxidase catalyst translocates from the extracellular space into nuclei of aortic smooth-muscle cells. Journal of Cell Biochemistry 79, 576-582.

Nonneman, D., Kappes, S. M. and Koohmaraie, M. 1999. Rapid communication: a polymorphic microsatellite in the promotor region of the bovine calpastatin gene. J. Anim. Sci 77, 3114-3115.

Slee, R. B., Hillier, S. G., Largue, P., Harlow, C. R., Miele, G. and Clinton, M. 2001. Differentiation-dependent expression of connective tissue growth factor and lysyl oxidase messenger ribonucleic acids in rat granulosa cells. Endocrinology 142, 1082-1089.

Terwilliger, J. D. 1995. A powerful likelihood method for the analysis of linkage disequilibrium between trait loci and one or more polymorphic marker loci. American Journal of Human Genetics 56, 777--787.

Whipple, G., Koohmaraie, M., Dikeman, M. E., Crouse, J. D., Hunt, M. C., Klemm, R. D. 1990. Evaluation of attributes that affect longissimus muscle tenderness in Bos taurus and Bos indicus cattle. J.Anim. Sci. 68, 2716-2728.

Woodward, B. W., DeNise, S. K., and Marchello, J. A. 2000. Evaluation of calpastatin activity measures in ante-and postmortem muscle from half-sib bulls and steers. J.Anim. Sci. 78, 804-809.

The invention claimed is:

1. A method for assessing the tenderness of meat from an animal, comprising the step of testing the animal for the presence of CAST3 D/E allele 1, 2 or 3, wherein the animal is bovine cattle,
wherein the presence of CAST3 D/E allele 2 or 3 indicative of greater meat tenderness in comparison to the presence of CAST3 D/E allele 1, and
wherein said CAST3 D/E alleles 1, 2 and 3 have the nucleotide sequences of SEQ ID NOS:1, 2 and 3, respectively.

2. A method for selecting an animal likely to yield meat of improved tenderness, comprising the steps of:
(1) testing the animal for the presence of CAST3 D/E allele 1, 2 and 3 ; and
(2) selecting animals which have the CAST3 D/E allele 2 or 3 ,
wherein the animals are bovine cattle, and
wherein said CAST3 D/E alleles 1, 2 and 3 have the nucleotide sequences of SEQ ID NOS:1, 2 and 3, respectively.

3. A method as claimed in claim 2 wherein the allele tested for is said CAST3 D/E allele 2 and cattle that are homozygous for this allele are selected.

4. A method as claimed in claim 3 further comprising the step of testing for the additional presence of one or more alleles selected from the group consisting of the CAST3 D/E allele 1 and CAST3 D/E allele 3.

5. A method as claimed in claim 1 further comprising breeding the selected animal.

6. A method for assessing the tenderness of meat from an animal, comprising the step of testing the animal for the presence of CAST3 D/E allele 1, 2 or 3, wherein the animal is bovine cattle selected from the group consisting of Hereford and Angus,
wherein the presence of CAST3 D/E allele 2 or 3 is indicative of greater meat tenderness in comparison to the presence of CAST3 D/E allele 1, and
wherein said CAST3 D/E alleles 1, 2 and 3 have the nucleotide sequences of SEQ ID NOS:1, 2 and 3, respectively.

7. A method for selecting an animal likely to yield meat of improved tenderness, comprising the steps of:
(1) testing the animal for the presence of CAST3 D/E allele 1, 2 or 3 ; and
(2) selecting animals which have the CAST3 D/E allele 2 or 3,
wherein the animals are bovine cattle selected from the group consisting of Hereford and Angus, and
wherein said CAST3 D/E alleles 1, 2 and 3 have the nucleotide sequences of SEQ ID NOS:1, 2 and 3, respectively.

8. A method as claimed in claim 7 wherein the allele tested for is said CAST3 D/E allele 2 and bovine cattle that are homozygous for this allele are selected.

9. A method as claimed in claim 8 further comprising the step of testing for the additional presence of one or more alleles selected from the group consisting of the CAST3 D/E allele 1 and CAST3 D/E allele 3.

10. A method as claimed in claim 7 further comprising breeding the selected animal.

* * * * *

SEQUENCE LISTING

```
<160> NUMBER OF SEQ ID NOS: 10

<210> SEQ ID NO 1
<211> LENGTH: 170
<212> TYPE: DNA
<213> ORGANISM: Bos sp.

<400> SEQUENCE: 1
catttggaaa acgatgcctc acgtgttctt cagtgttctg atttctcatg acccctttcc        60
tcttggactt gtgggactgt gtttgatgtt tccctgggtt gttgtttata agtcagtcat       120
aaaatactgt gcattgggca catgtctcct cttgagctgc taatcgtaga                  170

<210> SEQ ID NO 2
<211> LENGTH: 170
<212> TYPE: DNA
<213> ORGANISM: Bos sp.

<400> SEQUENCE: 2
catttggaaa acgatgcctc acgtgttctt cagtgttctg atttctcatg acccctttcc        60
tcttagactt gtgggactgt gtttgatgtt tccctgggtt gttgtttata agtcagtcat       120
aaaatactgt gcattgggca catgtctcct cttgagctgc taatcgtaga                  170

<210> SEQ ID NO 3
<211> LENGTH: 170
<212> TYPE: DNA
<213> ORGANISM: Bos sp.

<400> SEQUENCE: 3
catttggaaa acgatgcctc acgtgttctt cagtgttctg atttctcatg acccctttcc        60
tcttagactt gtgggactgt gtttgatgtt tccctgggtt gttgtttata agtcagtcat       120
aatatactgt gcattgggca catgtctcct cttgagctgc taatcgtaga                  170

<210> SEQ ID NO 4
<211> LENGTH: 329
<212> TYPE: DNA
<213> ORGANISM: Bos sp.

<400> SEQUENCE: 4
ttatcactga tgtcaaacct ggaaactata ttctcaaggt agagaacttt gaacatatac        60
ccataatgta tttcaattgt gactcagtgg gcttattctc tggagtcaaa tgttaaatat       120
```

```
tcatggtcct gcaaacaatt atacatcttc tagaactact tytaaaccaa cctagatata    180
ttwaaaaaat tcttatttga aacacatgcc taacttacac cctcttcctt gcctgattta    240
gttgaattat taaacactgc tgatgaaatc tgaaacacag atgatgtttg ttttgcctag    300
gtcagtgtga atcccagcta tttggtgcc                                      329
```

<210> SEQ ID NO 5
<211> LENGTH: 22
<212> TYPE: DNA
<213> ORGANISM: Artificial Sequence
<220> FEATURE:
<223> OTHER INFORMATION: castd probe

<400> SEQUENCE: 5

```
catttggaaa acgatgcctc ac                                              22
```

<210> SEQ ID NO 6
<211> LENGTH: 25
<212> TYPE: DNA
<213> ORGANISM: Artificial Sequence
<220> FEATURE:
<223> OTHER INFORMATION: caste probe

<400> SEQUENCE: 6

```
tctacgatta gcagctcaag aggag                                           25
```

<210> SEQ ID NO 7
<211> LENGTH: 26
<212> TYPE: DNA
<213> ORGANISM: Artificial Sequence
<220> FEATURE:
<223> OTHER INFORMATION: cast5U1 probe

<400> SEQUENCE: 7

```
gtaaagccgc acaaaacaca cccagg                                          26
```

<210> SEQ ID NO 8
<211> LENGTH: 29
<212> TYPE: DNA
<213> ORGANISM: Artificial Sequence
<220> FEATURE:
<223> OTHER INFORMATION: cast5D1 probe

<400> SEQUENCE: 8

```
gtttctggac cctctggatg aggaagcgg                                       29
```

<210> SEQ ID NO 9
<211> LENGTH: 20
<212> TYPE: DNA
<213> ORGANISM: Artificial Sequence
<220> FEATURE:
<223> OTHER INFORMATION: Lox K5 probe

<400> SEQUENCE: 9

```
tatcactgat gtcaaacctg                                                 20
```

<210> SEQ ID NO 10
<211> LENGTH: 20
<212> TYPE: DNA
<213> ORGANISM: Artificial Sequence
<220> FEATURE:
<223> OTHER INFORMATION: Lox K6 probe

```
<400> SEQUENCE: 10
actcaggcac caaatagctg                                                          20
```